United States Patent
Watson et al.

(10) Patent No.: US 7,291,309 B2
(45) Date of Patent: Nov. 6, 2007

(54) SAMPLE DISTRIBUTION APPARATUS/SYSTEM

(75) Inventors: Leslie Robert Watson, Queensland (AU); Christoph Friedrich Tschopp, Queensland (AU); Ross Andrew Weaver, Queensland (AU); Ian David Henderson, Somerset (GB); Pieter Adriaan Kuiper, Queensland (AU); Christian Darrel Decosterd, Sunnybank (AU)

(73) Assignee: A.i. Scientific Pty Ltd., Queensland (AU)

( * ) Notice: Subject to any disclaimer, the term of this patent is extended or adjusted under 35 U.S.C. 154(b) by 778 days.

(21) Appl. No.: 10/434,177

(22) Filed: May 9, 2003
(Under 37 CFR 1.47)

(65) Prior Publication Data
US 2004/0005245 A1    Jan. 8, 2004

Related U.S. Application Data

(62) Division of application No. 09/555,360, filed on Sep. 26, 2000, now Pat. No. 6,599,476.

(51) Int. Cl.
*G01N 21/13* (2006.01)
*B65C 9/18* (2006.01)
*B65B 51/10* (2006.01)

(52) U.S. Cl. .......................... 422/63; 422/65; 422/66; 422/67; 422/68.1; 156/542; 53/477; 53/478; 53/329.2

(58) Field of Classification Search .......... 422/63–104; 436/43, 49, 54, 174, 180; 73/863.32, 864.01, 73/864, 864.14, 864.31, 863.24, 863.25; 156/540, 542, 378–379; 53/478, 329.2
See application file for complete search history.

(56) References Cited

U.S. PATENT DOCUMENTS

| | | | |
|---|---|---|---|
| 4,039,288 A | | 8/1977 | Moran |
| 4,194,341 A | * | 3/1980 | Kihnke et al. ............... 53/282 |
| 4,585,497 A | * | 4/1986 | Webster ..................... 156/69 |
| 4,824,642 A | * | 4/1989 | Lyman et al. ............. 422/100 |
| 4,835,707 A | * | 5/1989 | Amano et al. ............ 700/266 |
| 4,849,176 A | | 7/1989 | Sakagami |
| 4,855,110 A | | 8/1989 | Marker et al. |
| 5,104,808 A | | 4/1992 | Laska et al. |
| 5,176,880 A | | 1/1993 | Iwasaki et al. |
| 5,209,903 A | | 5/1993 | Kanamori et al. |
| 5,405,482 A | * | 4/1995 | Morrissette et al. ........ 156/364 |
| 5,431,201 A | | 7/1995 | Torchia et al. |
| 5,443,791 A | | 8/1995 | Cathcart et al. |
| 5,455,006 A | | 10/1995 | Aota et al. |
| 5,456,882 A | | 10/1995 | Covain |

(Continued)

FOREIGN PATENT DOCUMENTS

AU    23658/84    8/1984

(Continued)

*Primary Examiner*—Brian R. Gordon
(74) *Attorney, Agent, or Firm*—Young & Thompson

(57) ABSTRACT

A pathology distribution system 10 is provided for automated sample container 14, 15 distribution. The system 10 comprises a loading station 500 for loading samples in primary containers 14 of different types, a sample handling station 16 for receiving the containers 14 and identifying the container types and samples therein, and a container distribution station 38 for distributing the containers in areas or racks in the distribution station 38 marked for analyzing processes prescribed for the samples therein.

32 Claims, 24 Drawing Sheets

U.S. PATENT DOCUMENTS

| | | | |
|---|---|---|---|
| 5,472,669 A | 12/1995 | Miki et al. | |
| 5,497,670 A * | 3/1996 | Carl | 73/863.32 |
| 5,498,543 A | 3/1996 | Berndt | |
| 5,528,879 A * | 6/1996 | Louy et al. | 53/201 |
| 5,584,161 A * | 12/1996 | Zanini et al. | 53/317 |
| 5,614,415 A | 3/1997 | Markin | |
| 5,665,601 A * | 9/1997 | Kilmer | 436/54 |
| 5,687,552 A * | 11/1997 | Barca | 53/490 |
| 5,785,798 A * | 7/1998 | Horsman et al. | 156/361 |
| 5,798,035 A | 8/1998 | Kirk et al. | |
| 5,897,835 A | 4/1999 | Seaton et al. | |
| 5,940,178 A | 8/1999 | Barber et al. | |
| 5,948,360 A | 9/1999 | Rao et al. | |
| 5,966,309 A * | 10/1999 | O'Bryan et al. | 700/225 |
| 5,985,215 A | 11/1999 | Sakazume et al. | |
| 6,060,022 A | 5/2000 | Pang et al. | |
| 6,090,630 A | 7/2000 | Koakutsu et al. | |
| 6,117,683 A | 9/2000 | Kodama et al. | |
| 6,120,733 A | 9/2000 | Goodman et al. | |
| 6,143,573 A | 11/2000 | Rao et al. | |
| 6,190,617 B1 * | 2/2001 | Clark et al. | 422/104 |
| RE37,194 E | 5/2001 | Kirk et al. | |
| 6,350,412 B1 | 2/2002 | Williams et al. | |
| 6,387,327 B1 | 5/2002 | Ricci et al. | |
| 6,498,037 B1 * | 12/2002 | Carey et al. | 436/50 |
| 2002/0031446 A1 | 3/2002 | Friedlander et al. | |

FOREIGN PATENT DOCUMENTS

| | | |
|---|---|---|
| AU | 16756/88 | 12/1988 |
| AU | 35096/84 | 4/1995 |
| EP | 0 243 915 | 11/1987 |
| JP | 08-198226 | 8/1996 |
| JP | 08-334515 | 12/1996 |
| WO | WO83/00393 | 2/1983 |
| WO | WO92/08987 | 5/1992 |

* cited by examiner

SAMPLE DISTRIBUTION APPARATUS/SYSTEM

This application is a division of our previously application Ser. No. 09/555,360, filed Sep. 26, 2000, and now U.S. Pat. No. 6,599,476.

FIELD OF INVENTION

THIS INVENTION relates to a pathology sample distribution apparatus/system and in particular but not limited to an automated pathology specimen tube distribution apparatus/system for use in medical pathology laboratories.

BACKGROUND ART

In pathology industries samples from different sources need to be analysed for different reasons. Some of the samples may also need to be split or apportioned for multiple analysis. It is desired to automate the distribution systems for these samples so that there is minimum human involvement in the distribution.

For example, the collection and analysis of samples including pathology specimens such as blood involve numerous steps which are prone to human errors could result in disastrous consequences for both the medical laboratory and the patients concerned. One fundamental area where such errors can occur is the transfer of the specimen from primary specimen tubes containing the specimen first collected from a patient to secondary sample tubes which thereby contain aliquot of the specimen for actual analysis by an analysing instrument. Major problems occur where the tubes are incorrectly labelled or the tubes are of an incorrect type for a particular test specifically requisitioned by a physician. In order to solve these and other problems, most pathology laboratories have in place numerous time consuming manual checking procedures. As a consequence of the advent of highly contagious and dangerous diseases such as AIDS and hepatitis and advances in computer technology, much of the organisation and transfer of the secondary sample tubes to racks or holders for the purpose of analysis is now substantially automated. The whole process is often monitored to an extent such that an enquiry of the computer system involved will reveal the location of the primary specimen tubes and/or secondary sample tubes at any stage of the tube management and analytical process.

Invariably, pathology specimen distribution centres are often placed invidiously in what can only be described as a "meat in the sandwich" situation. This may be given by way of example where a distribution centre has to decide which test is appropriate when the full spectrum of test procedures is not known or understood by a referring physician, or, when a scientist responsible for the analytical procedures has not clearly spelt out to specimen collecting staff what type and amount of specimen are required. This situation is often resolved by obtaining further specimens from the patient.

This practice is wasteful of time and resources such as disposable and extra specimen tubes or containers. The possibility of errors in such situations is often further compounded by the limitations of the laboratory's computer information management system (LIMS) which is only as accurate as the information provided to it.

Many laboratories continue to employ a manual specimen tube management system because their primary focus is in the analysis of samples and the actual reporting of the analysis results. Unless the laboratory has an automated specimen distribution system, human errors can easily occur in any manual specimen tube management system which are often to the detriment of other areas of the analysis. As a consequence of the absence of an accurate and fail safe tube management system, it may be impossible to know if a correct specimen type has been collected until it is delivered to the scientist at the analyser. The scientist will also have to decide at this stage whether a sufficient volume of the sample has been collected for the particular analysis and whether or not the sample, for example if it is blood, is too haemolysed or clotted for a particular test to be carried out. As a result many of the errors found in laboratories have their origin at the specimen distribution centre and such errors become compounded as the laboratory process continues. Further the absence of automated tube management systems often leads to inefficient manual sample storage facilities resulting in the misplacement of samples received so that the result obtained if inconsistent with what is expected has to be rechecked by re-running the test against a reference source to verify the particular infection. In laboratories where there are no reliable sample storage systems, there is usually a proliferation of various systems which are not under computer control resulting in unnecessary costs including resources and consumables for further tests as mentioned above.

In attempting to identify these and other problems, the applicant has listed a number of deficient areas found in current manual systems and those systems necessarily involving other instruments and tests. Some of these deficiencies include the transportation of uncapped primary and secondary tubes resulting in the increased possibility of contamination. The fact that the same specimen can be collected in different tube types having different colour coded caps can also result in confused or erroneous readings by instruments or staff unfamiliar with a particular manufacturer's colour coding scheme.

In addition, the presence of different cap types and different clot activating substances being used by different physicians for collected blood specimens can cause the laboratory to restrict itself to one collection tube manufacture in the interest of eliminating errors.

Furthermore, the particular tube transport mechanism associated with a specific test often dictates the design of the laboratory and results in restricting the tube management system to one analysis type only.

Other limitations include the inability to distribute samples from one collection resulting in multiple collections of the same specimen type where it is necessary to repeat the same test or where other tests on the same type of specimen are involved.

Known attempts to overcome certain of the above problems include a number of systems presently in operation which may be broadly categorised as follows:
1. An existing manually controlled system is modified by taking advantage of various analysers that are capable of bar code reading and manually interfacing them with the laboratory's existing computer information management system based on bar coding. This has often resulted in the collection of more specimens from the patients in order to distribute each separate collection tube to a specific analyser resulting in a wastage of specimen and problems associated where a great number of tubes have to be handled, for example, misplacement of sample tubes, accidental spillage and contamination.
2. Systems which utilise a conveyor belt that transports the collected specimen tubes to an appropriate work station where a tube is captured and acted upon by a number of processes inclusive of picking up the tube and putting it in a storage rack. The system then recaps the specimen tubes and transports the capped tubes to their destination. In this system there is no computerised management system so that each laboratory has to write its own manually controlled management system in respect of the whole process.

3. Systems which utilise the conveyor belt system but are limited by utilising one manufacturer's specimen tube type only. This system processes the specimen by the tipping the collection tube in an inverted position, inserting a disposable plastic device into the specimen tube and then pumping in air to expel a sample of the specimen to a secondary tube of a certain type.
4. Systems which use a robotic arm to uncap and distribute specimen tubes in which the primary specimen is collected without any distribution or transfer of sample amounts or aliquot to secondary tubes.
5. Systems which utilise a needle to pierce the cap of the primary specimen tube and distribute sample aliquot to unlabelled and uncapped secondary tubes in a rack that holds all the tubes associated with the particular primary specimen tube.

Specific problems which have been identified by the applicant associated with the prior art systems described above include the following:

1. Conveyor belt systems are large and bulky and often cut across doorways and require major remodelling and restructuring of the laboratory.
2. Prior art tube distribution systems are often restricted to primary specimen tubes and secondary sample tubes of a certain type or make. Where specimen and/or sample tubes are of types different from the type associated with the particular prior art system, breakages of the tubes during processing can occur and thereby resulting in the loss of the specimen and/or contamination of the apparatus.
3. There is often an absence of an on board computerised tube monitoring facility to keep track of the physical status of the tubes. If the tubes are left uncapped, the systems can result in exposure of the uncapped tubes causing contamination of the sample as well as the laboratory environment.
4. Systems where the available sample volume is not measured prior to the aspiration of the sample resulting in the situation that multiple samples cannot be obtained from the single specimen. For example where one tube of blood is insufficient for the battery of tests requested and therefore two or more samples have to be further collected from the patient.
5. Systems which are restricted to certain types of specimens such that the systems are not able to cope with specimens of serum, plasma, urine and other fluids from a single patient.
6. Systems where the recapping of primary specimen tubes are made with another cap resulting in higher running costs and design constraints which may result in spillage and the possibility of contamination when a tube is broken or dropped due to the extra handling of the tube associated with the recapping process.
7. A restriction on rack types or holders required by separate analysing instrument systems.
8. The absence of systems where there is an automated labelling of the secondary sample tubes resulting in an increased chance of human errors.
9. Systems where the cost effective sealing of secondary tubes by the use of plastic laminate instead of caps is not provided for.
10. Systems which cannot identify the physical characteristics of a particular specimen tube and/or the specimen in the tube prior to processing.
11. Systems which cannot process more than one type of primary specimen tube or secondary sample tube as previously described.

OBJECT OF THE INVENTION

It is therefore an object of the present invention to alleviate to some degree one or more of the abovementioned problems associated with prior art sample distributors presently in operation.

SUMMARY OF THE INVENTION

In one aspect therefore the invention resides in a sample container handling apparatus for a pathology sample distribution system having a plurality of containers of different types and the containers each containing a sample for pathology analysis and an identification indicator for the sample. The apparatus comprises a container handling station arranged for receiving the containers in turn. The handling station includes a container identification means for obtaining one or more characteristics of a container presented for identification and identifying the container type by comparing the obtained characteristic or characteristics with predetermined characteristics of the container types. A container type is identified when the obtained characteristic or characteristics match or are within a predetermined range from matching one or one set of the predetermined characteristics. The handling station also includes a sample identification means for identifying the sample by obtaining the identification indicator on the presented container. The obtained sample identification is used for the pathology analysis prescribed for the sample.

Preferably the container identification means is an image analyser. The image analyser may have a digital camera for capturing an image containing the one or more characteristics of the container and a light source for illuminating the container. Said one or more characteristics may include a dimension or dimensions of the container, one or more areas of the container and the colour of the cap of the container.

More preferably the image analyser is arranged to detect the level of the sample. In this regard the handling station is provided with a controller which controls a rotatable container receiving means for positioning the container so that a window in the container allowing the sample to be visible externally is positioned before the image analyser. Desirably the sample identification means produces a signal to the controller when the sample identification indicator is detected and the controller in turn stops the container at a predetermined position so that the window is before the analyser.

The image captured through the window is conveniently employed for determining the level and/or volume of the sample available for analysis.

In preference the sample identification means is a bar code scanner and the sample identification indicator is a bar coded label fixed to the container.

In a second aspect therefore the present invention resides in a sample container handling apparatus for a pathology sample distribution system having a plurality of containers and the containers each containing a sample for pathology analysis. The apparatus comprises a container distributor having a cap removal and replacement means. The cap removal and replacement means includes a container holder movable with respect a rotatable cap engagement and removal means. In operation a capped container positioned in the holder which is controllably moved towards the cap engagement and removal means. The cap engagement and removal means includes jaw members arranged to grip onto the cap and rotate the cap as the holder moves away from the cap engagement and removing means thereby uncapping the container. Replacement of the cap is enabled by moving the uncapped container towards the cap gripped by the jaw members and the cap engagement and removal means rotates the jaw members and thereby rotating the cap as the container is pushed onto the cap.

In a third aspect therefore the present invention resides in a sample container handling apparatus for a pathology sample distribution system having a plurality of containers and the containers each containing a sample for pathology analysis. The apparatus comprises a container distributor having sample aspiration and/or dispensing means for aspirating and/or dispensing volumetrically a predetermined portion of the sample in or to a container. The sample aspiration and/or dispensing means includes a pipette tip holder for holding a plurality of pipette tips, a pipette probe, an articulated arm arranged for removing a pipette tip from the holder and place the pipette tip on the probe, and a pipette tip removing means to remove the pipette tip from the probe for deposition in a disposal receptacle.

In a fourth aspect the present invention resides in a sample container handling apparatus for a pathology sample distribution system having a plurality of containers and the containers each containing a sample for pathology analysis. The apparatus comprises a blockage detection means for detecting blockage of flow in a sample aspiration means including a pipette tip for aspirating volumetrically a pre-determined portion of a samples in a container. A pipette tip controller is arranged to move the tip towards the sample in the container. The blockage detection means includes a pressure sensitive module having a pump for aspiration of the sample through the tip. The blockage detection means is arranged to detect blockage in the tip and thereby to provide a warning signal and to cause the operation of the sample aspiration means to be arrested until the blockage has been resolved.

The station also has a sample level detection means which includes a low pressure generating means for applying low pressure to the aspiration means, pressure sensor means for sensing the pressure in the aspiration means and an actuator for moving the tip towards the sample. The sample level is detected when the pressure as sensed by the sensor means exceeds a predetermined margin from a fixed pressure.

In a fifth aspect the present invention resides in a sample container handling apparatus for a pathology sample distribution system having a plurality of containers and the containers each containing a sample for pathology analysis a pathology specimen tube distributor. The apparatus comprises container sealing means for sealing containers with samples dispensed therein. The container sealing means includes a source of heat sensitive laminate tape; means for punching the tape to form caps for the containers; means for placing each said caps over the top of a container and means for heating the cap over the container to cause the laminate to seal the container.

The laminate tape preferably is dispensed from spools or reels.

In a sixth aspect of the present invention resides in a sample container handling apparatus for a pathology sample distribution system having a plurality of containers and the containers each containing a sample for pathology analysis. The apparatus comprises automatic labelling means for the application of adhesive labels to containers with samples dispensed therein. The automatic labelling means includes one or more spools of adhesive labels, means to provide sample identification indicators on the adhesive labels; a sample identification means to verify that the indicators on the labels corresponds to the indicators of containers from which the samples are aspirated, and means for detecting errors in the indicators on the labelled containers or the absence of a label.

In a seventh aspect the present invention resides in a sample container handling apparatus for a pathology sample distribution system having a plurality of containers for pathology analysis, each container having a closed end and an open end. The apparatus comprises hopper means for receiving and delivering one or more of the containers, and having container alignment means for aligning the containers from any position to a vertical position with the open ends positioned to receive samples.

Preferably the container alignment means includes a rotary magazine having circumferentially located compartments to hold horizontally positioned containers, a sideways plunger member arranged in co-operation with the magazine and a guide positioned beneath the magazine to change the position of the containers released from the magazine from the horizontal to the vertical position. In operation the plunger member pushes a closed end of a container so that the displaced container released from the magazine falls into the guide in the vertical position. Said co-operating plunger member when not in contact with a closed end, does not push a container which when released, falls into the guide in the vertical position.

In an eighth aspect the present invention resides in a pathology sample distribution system having a plurality of containers of different types and the containers each containing a sample for pathology analysis a pathology specimen. The system comprises a loading station for loading said containers, a container handling station arranged to receive the containers in turn from the loading station, and distribution station with areas or distribution holders marked for specific analysing processes. The handling station has one or a combination of two or more of the apparatus as described above.

In a ninth aspect therefore the present invention resides in a sample container handling apparatus for a pathology sample distribution system having a plurality of containers and the containers each containing a sample for pathology analysis. The apparatus comprises a loading station having a conveyor arrangement for conveying the containers in position to be loaded onto a tube handling station. The conveyor arrangement includes a movable conveyor surface on which carriers for carrying said containers can be placed. The conveyor surface has a first section arranged with a barrier dividing said first section into a buffer zone and a by-pass passage for the carriers. The buffer zone has an entrance and a diversion part is arranged adjacent to the entrance. In operation the diversion part diverts carriers carrying containers into the buffer zone and empty carriers continue to move into the by-pass passage.

Preferably The diversion part is arranged so that when the buffer zone is full of carriers carrying tubes, other carriers with or without tubes continue to move into the by-pass passage.

It is desired that buffer zone has a controllably actuable member positioned opposite to said entrance and the actuable member is controlled to push a carrier out of the buffer zone. Typically the actuable member is actuated when the container on a carrier has been loaded onto the handling station or a rejected tube is placed on a carrier in the buffer zone.

The conveyor surface may also have a second section arranged with a barrier dividing said second section into a reject zone for receiving carriers with rejected containers and a by-pass passage for other carriers. The reject zone has a diversion part arranged to divert carriers carrying rejected containers into the reject zone and to allow empty carriers continue to move into the reject zone by-pass passage.

In a tenth aspect therefore the present invention resides in a pathology sample distribution system having a plurality of containers of different types and the containers each containing a sample for pathology analysis. The system comprises:

primary container identification means; the identification means including a bar code scanner to scan bar coded labels and an image analyser to analyse one or more characteristics of the container and/or the sample in therein;

primary container cap removal and replacement means;

hopper means having container alignment means for delivering secondary containers each with a closed end and an open end in a vertical position and with the open ends in position to receive samples;

sample aspiration and/or dispensing means for aspirating and/or dispensing volumetrically proportions of the samples from the primary container;

blockage detection means for detecting blockage of flow in the sample aspiration means;

secondary container sealing means;

secondary container labelling means;

secondary container storage means;

container conveyance means;

wherein in operation each primary container containing a sample is presented to the identification means and the container is accepted or rejected according to given criteria; the identification means being arranged to reject a container when it fails to detect the given criteria and thereby indicating the presence of an error condition, when the given criteria are detected the cap of the primary container is removed and aliquots of the sample aspirated by the sample aspiration and/or dispensing means are dispensed to the secondary container or containers which are then sealed and labelled and placed in the storage means; and whereby the conveyance of the primary containers and secondary containers between operational steps is via the container conveyance means and the whole process is coordinated and controlled by a computerised laboratory information management system.

Suitably the primary container identification means is a receptacle for placing a capped primary container, and has a bar code scanner for scanning a bar coded label on the container and an image analyser for analysing the colour of the cap of the container, the diameter, height and shape characteristics of the container as well as the type and height of each layer of the sample in the container.

Preferably the given criteria by which the primary container is accepted or rejected by the identification means includes the following criteria.

1. Is the primary container bar code present?
2. Is the presented primary container appropriate for the tests requested?
3. What type of container is being presented?
4. Does the container need to be sampled?
5. What is the available sample volume?
6. What is the height restriction for a pipette tip to aspirate the sample?
7. What speed should the pipette travel to maintain its tip just below the surface of the sample during the aspiration process?
8. What secondary containers have to be generated?
9. What information has to be present on each label of the secondary containers?
10. What destination rack is associated with the primary container and the or each secondary container?
11. What is the order of filling the rack?
12. What spaces have to be left on the rack so that standards and controls can be later added?
13. Is the rack able to be removed?

Error conditions associated with accepting or rejecting a primary container include:

1. The bar code is not recognised by the laboratory computerised management system.
2. The bar code is unreadable.
3. The incorrect sample has been presented.
4. There is insufficient sample volume in the container for the required test which may be overridden in the case of multiple sample collections.
5. There is a restriction to flow in the sample aspiration and/or dispensing means. For example if the sample is blood and the blood has clotted, or the sample is too viscous or there is a jam in the hardware of the system.

Preferably the rack design incorporates its own unique bar code identifiers so that coordinated storage systems can be utilised as well as being completely traceable at any stage of the process.

Preferably the information on the bar code is unique to each patient episode and the collected samples or specimens. This bar code can be used to identify and locate all the secondary containers associated with the relevant primary container.

Preferably the acceptance or rejection of and error condition associated with a primary container is displayed on electronic display means and/or printed means.

Suitably the container cap removal and replacement means is a robotic arm having a specially adapted member to remove and replace the cap of a container.

Preferably the one or more secondary containers are plastic tubes and may have different volumes and shapes.

Preferably the sample aspiration and/or dispensing means has means adapted to remove and dispose of used pipette tips.

Preferably the container storage means are racks for holding multiple containers.

Preferably the computerised laboratory information management system is an integral part of the apparatus however may be an already existing system to which the pathology specimen tube distributor is interfaced.

Preferably the container conveyance means is a continuous conveyer belt on which the containers may be placed in holding stands or racks. Alternatively, a robotic tray may be used for the same purpose.

DETAILED DESCRIPTION OF DRAWINGS

Figure 1:
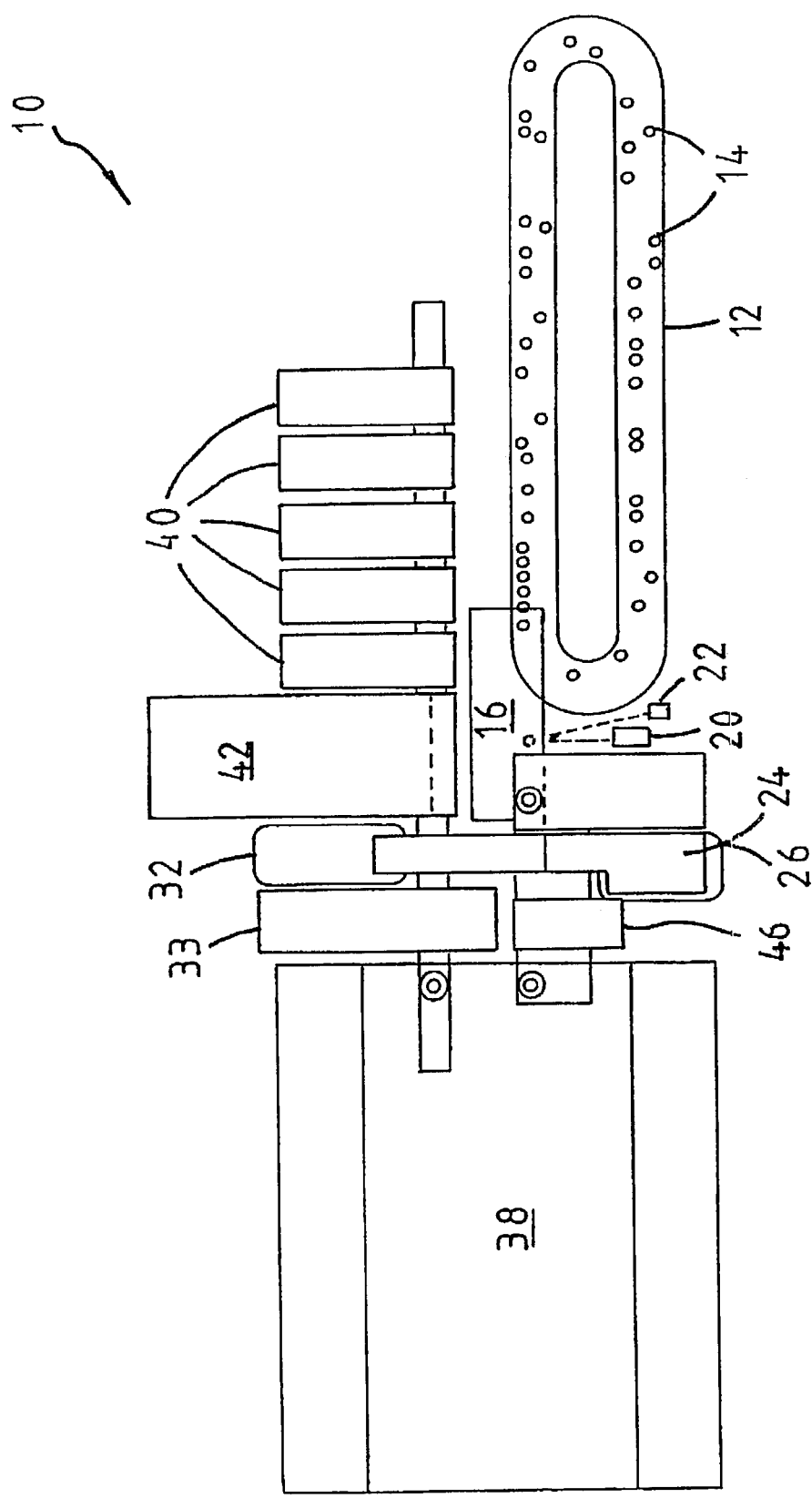
FIG. 1 shows a schematic plan view of an embodiment of the system according to the invention.

It can be seen in the overview of the system shown in FIG. 1 that the pathology specimen tube distribution system 10 according to an embodiment of the present invention comprises a loading station having a looped tube conveyer belt 12 on which are placed primary specimen tubes 14 in carriers or pucks 190 (to be described with reference to FIGS. 11 to 17). The primary specimen tubes 14 pass through a tube and sample identification arrangement of a tube handling station also known as the presented tube handler 16 having specimen tube receiving and identification means. Each specimen tube 14 for use in the system 10 has a bar code sticker 88 (see FIG. 2) affixed adjacent to an area or window of the tube 14 which allows the sample therein to be visible externally thereof. The primary specimen tubes 14 are rotated for bar code reading by a bar code reader 20. On reading the bar code, a signal is sent to a controller (not shown) which stops the rotation so that the visible window of the tube 14 is presented for images of the tube 14 to be captured for image analysis by an image analyser 22 which in this embodiment is a digital camera.

Accurate quantities of samples are then automatically aspirated at an aliquoting arrangement having an aliquot bridge 24 which incorporates the sample aspiration and dispensing means 86 (to be described later). Associated with the aliquot bridge 24 is a pipette hopper 26 from which disposable pipette tips 28 (see FIG. 5) are automatically loaded onto a probe 30 (see FIG. 5) in turn and soiled pipette tips 28 are disposed into a bin 32. The primary specimen tubes 14 are then recapped with their original caps 34 (see FIG. 3) and transported to a holding area having a holder 46 from which they are picked up by a robotic arm (not shown) and placed in racks (not shown) in a distribution station 38 associated with the robotic arm.

The secondary sample tubes 15 (see FIG. 6) which are loaded from secondary sample tube hoppers 40 pass through a tube labelling arrangement having an automatic label printer and labeller 42. The labeller 42 applies labels to the secondary sample tubes 15 (see FIG. 6) with information corresponding to information associated with the primary specimen tubes 14. The secondary sample tubes 15 are then filled with the samples aspirated from the primary specimen tubes 14 before being capped with laminated caps 44 (see FIG. 7) by the capper 33 in a capping arrangement. The labelled and capped secondary sample tubes 15 are then transferred by a robotic arm (not shown) to racks (not shown) which are also placed in the distribution station 38.

Figure 2:
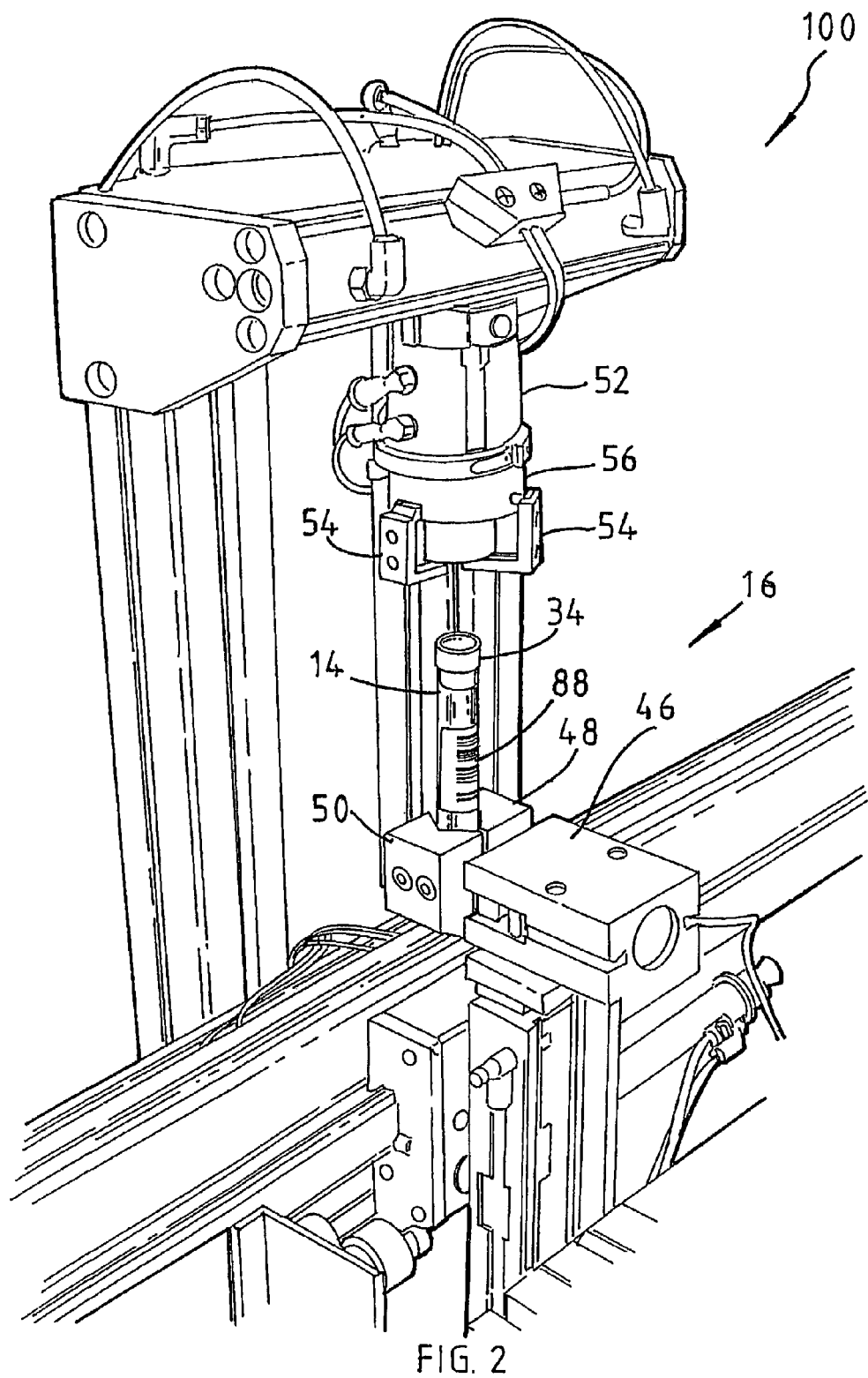
FIG. 2 shows an embodiment of the apparatus for decapping and recapping the primary specimen tubes for the system according to the invention.

FIG. 2 shows the apparatus 100 which is responsible for decapping and recapping the primary specimen tubes 14 presented to it. As shown the primary specimen tube 14 is held between the grippers 48, 50 of the tube handler 46. The decapping and recapping head 52 has pneumatically operated jaws 54 coupled to a rotatable part 56 which allows the jaws 54 to move laterally and to be rotated 360°. Due to the lateral movement the head 52 can decap and recap different caps 34 of different sizes and types with the same action. The types of caps including rubber bungs, plastic covered bungs and screw caps.

Figure 3B:
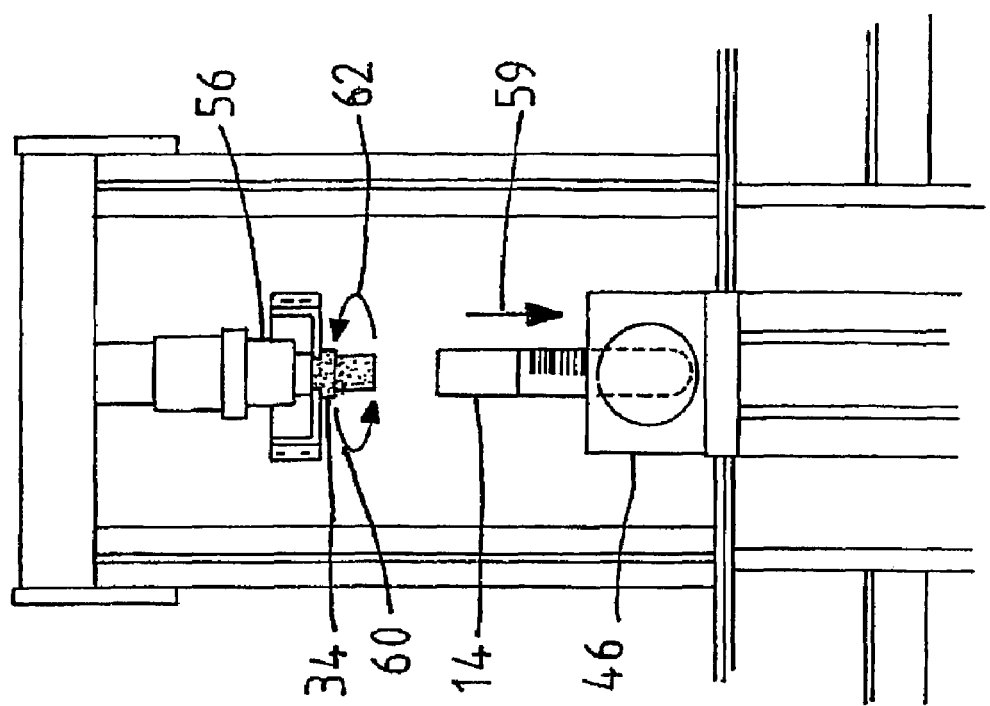
FIG. 3A and FIG. 3B show side elevations of the apparatus of FIG. 2.
Figure 3A:
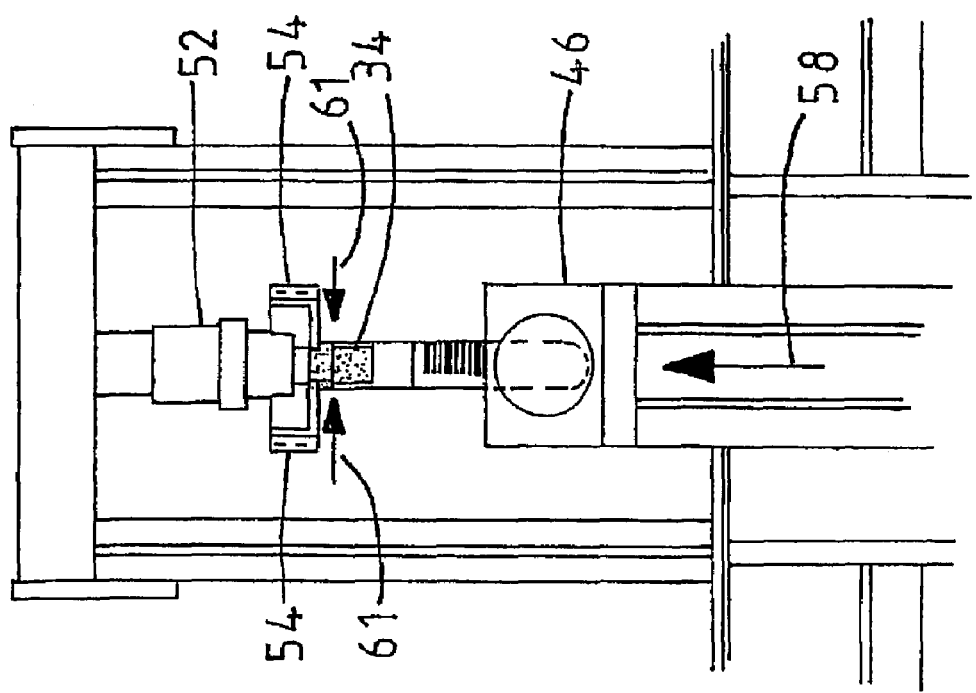

FIG. 3A and FIG. 3B are side elevations showing the decapping and recapping head 52 of FIG. 2 engaging the cap 34 of the primary specimen tube 14. The primary specimen tube 14 is pushed in the direction of the arrow 58 by the tube handler 46 onto the decapping and recapping head 52 wherein the jaws 54 move radially inward as shown by the arrows 61 to engage the upper portion of the cap 34. The rotatable part 56 causes the jaws 54 to rotate 360° shown by arrows 60, 62 while at the same time the primary specimen tube 14 is pulled downwards as shown by arrow 59 away from the cap 34 by the tube handler 46. This results in the removal of the cap 34 from the primary specimen tube 14.

The recapping of the primary specimen tube 14 is the reverse of the decapping process wherein the specimen tube 14 is pushed back onto the rotating cap 34 which prevents pressuring the tube 14.

Figure 4:
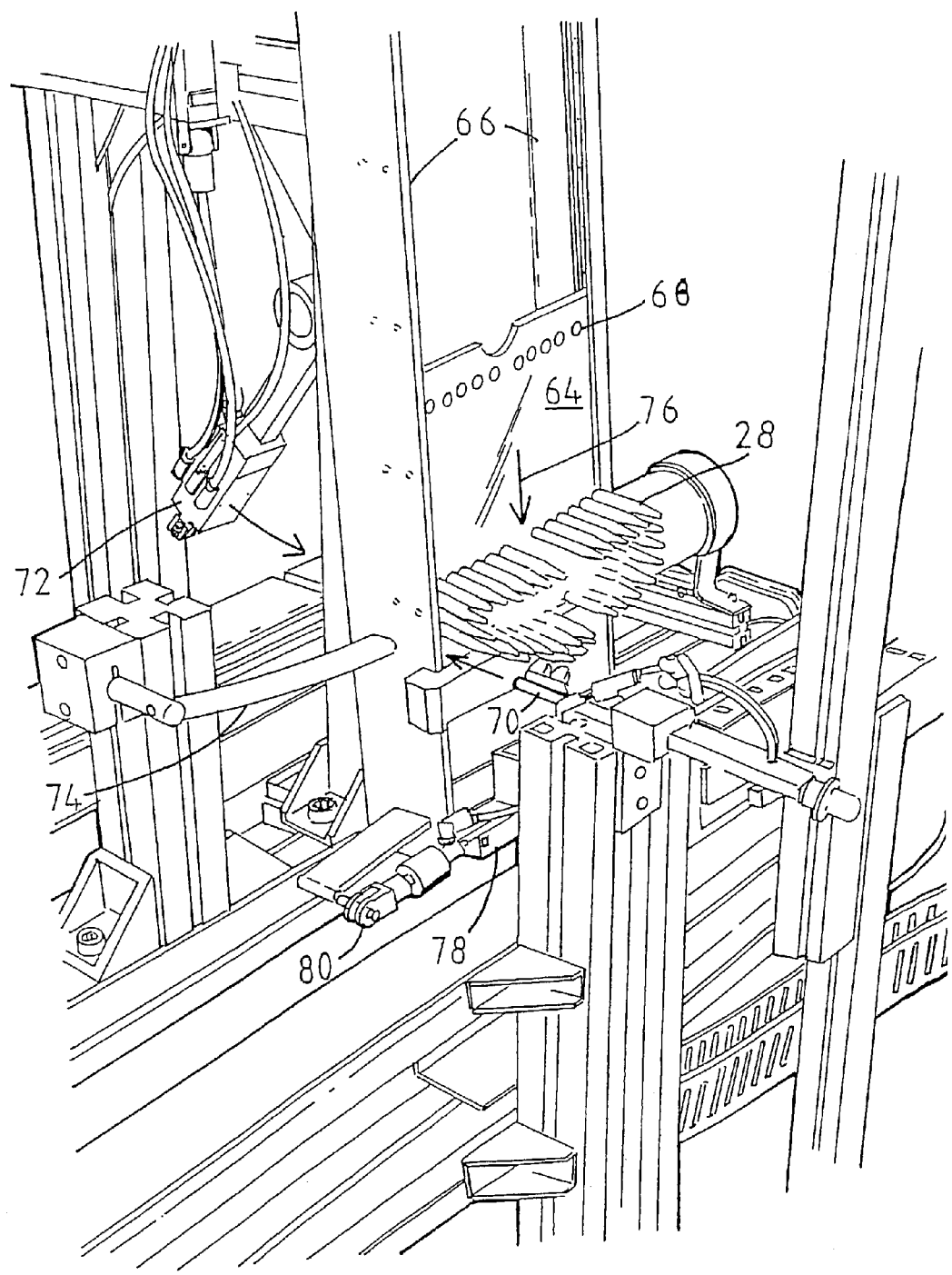
FIG. 4 shows details of an embodiment of the pipette hopper illustrated in FIG. 1.

FIG. 4 shows detail of the pipette hopper 26 illustrated in of FIG. 1. There is shown detail of a pipette tip holder 64 holding rows of pipette tips 28. The holder 64 slides in a frame 66 which allows the pipette tip holder 64 to move both horizontally and vertically. The pipette tips 28 are pushed out of the holes 68 by a pneumatic plunger 70 by movement in the direction to a pipette arm 72. As a pipette tip 28 is pushed out of its hole 68 in each row a stopper bar 74 which passes through the frame 66 engages the next pipette tip 28 which is moved into the correct position for the plunger 70 to push it out. On the exhaustion of all the pipette tips 28 in a row the pipette tip holder 64 moves downwards as shown by arrow 76 until the next row of pipette tips 28 is in position for the plunger 70. The operations of the pipette tip holder 64 and movement of the frame 66 in relation to the plunger 70 are governed pneumatically. The movement of the frame 66 is via the pneumatic actuator 78 operating on a clevis pin assembly 80.

Figure 5:
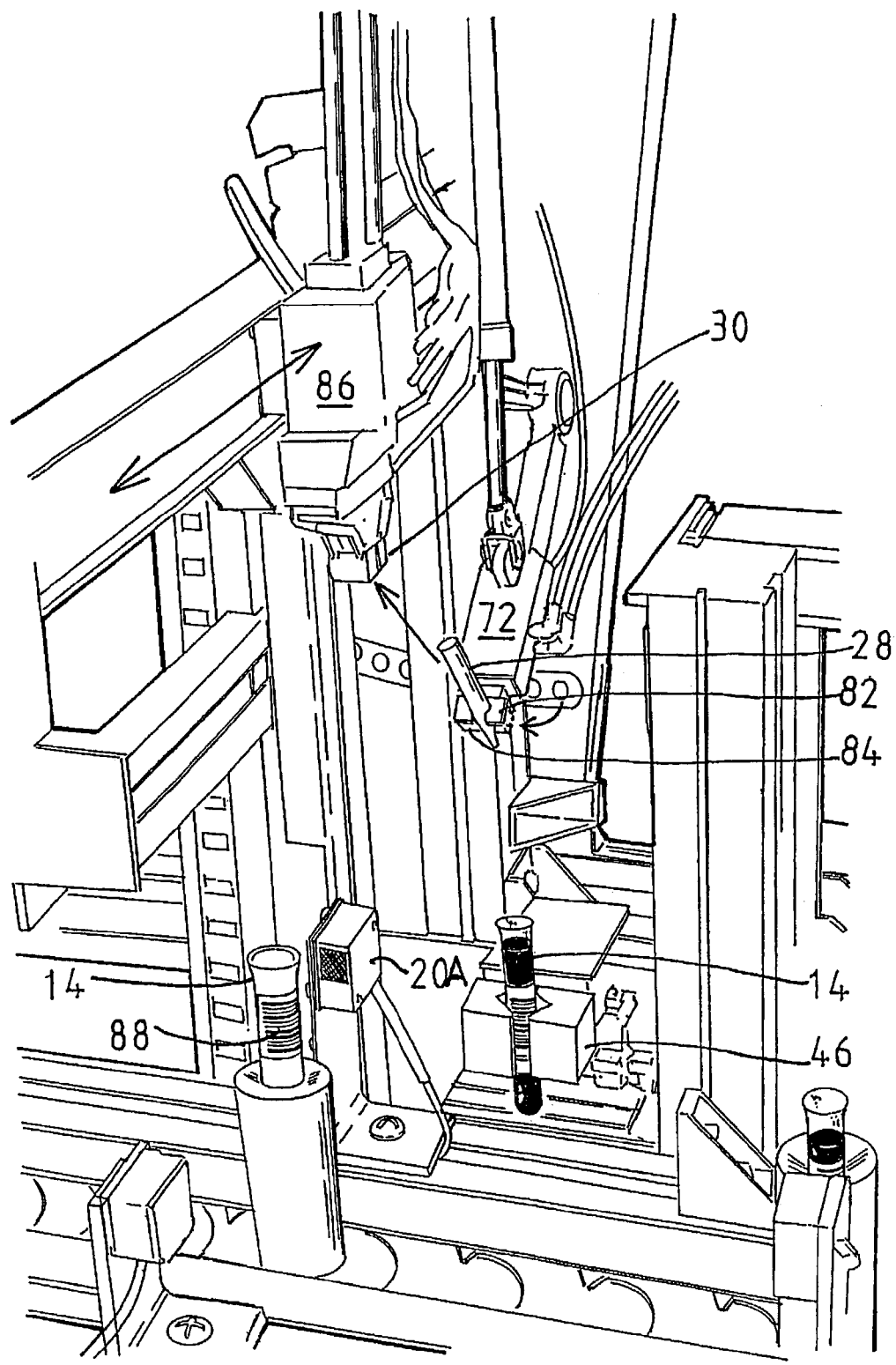
FIG. 5 shows details of the pipette arm illustrated in FIG. 4.

FIG. 5 shows detail of the pipette arm 72 illustrated in FIG. 4. A pipette tip 28 located in the jaws 82, 84 of the pipette arm 72 is placed over a probe 30 of the sample aspiration and dispensing means 86. Also shown in FIG. 5 is a primary specimen tube 14 held in the tube handler 46. There is also shown an optical sensor 20A to detect whether a specimen tube 14 is at the preset position.

Figure 6A:
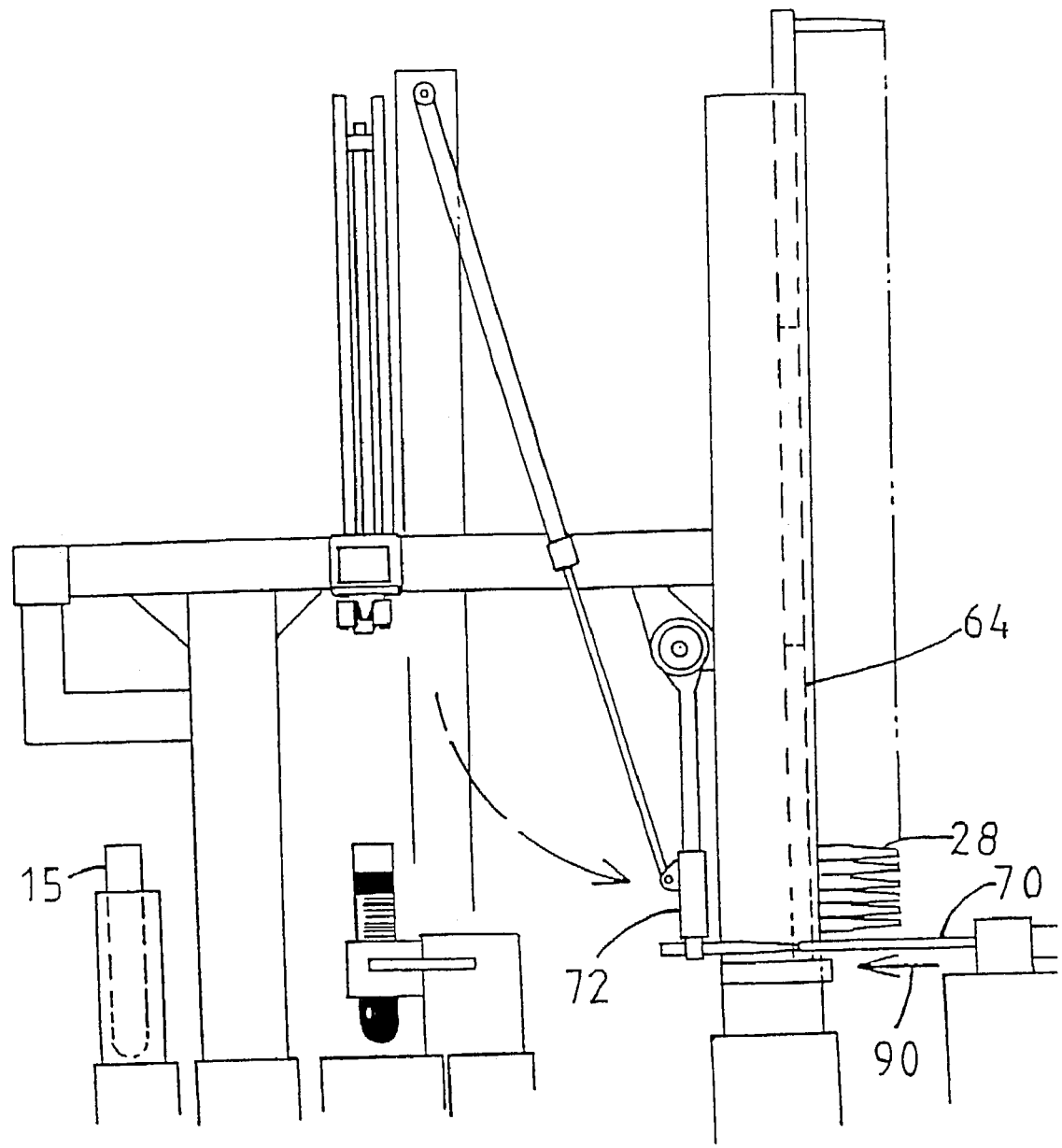
FIG. 6A and FIG. 6B show the operation of the pipette arm of FIG. 5.

FIG. 6A shows a side elevation of the action of the pipette arm 72 illustrated FIG. 5. The pipette arm 72 engages a pipette tip 28 which has been pushed in the direction of arrow 90 by the plunger 70 from a hole 68 in the pipette tip holder 64 holding rows of pipette tips 28.

Figure 6B:
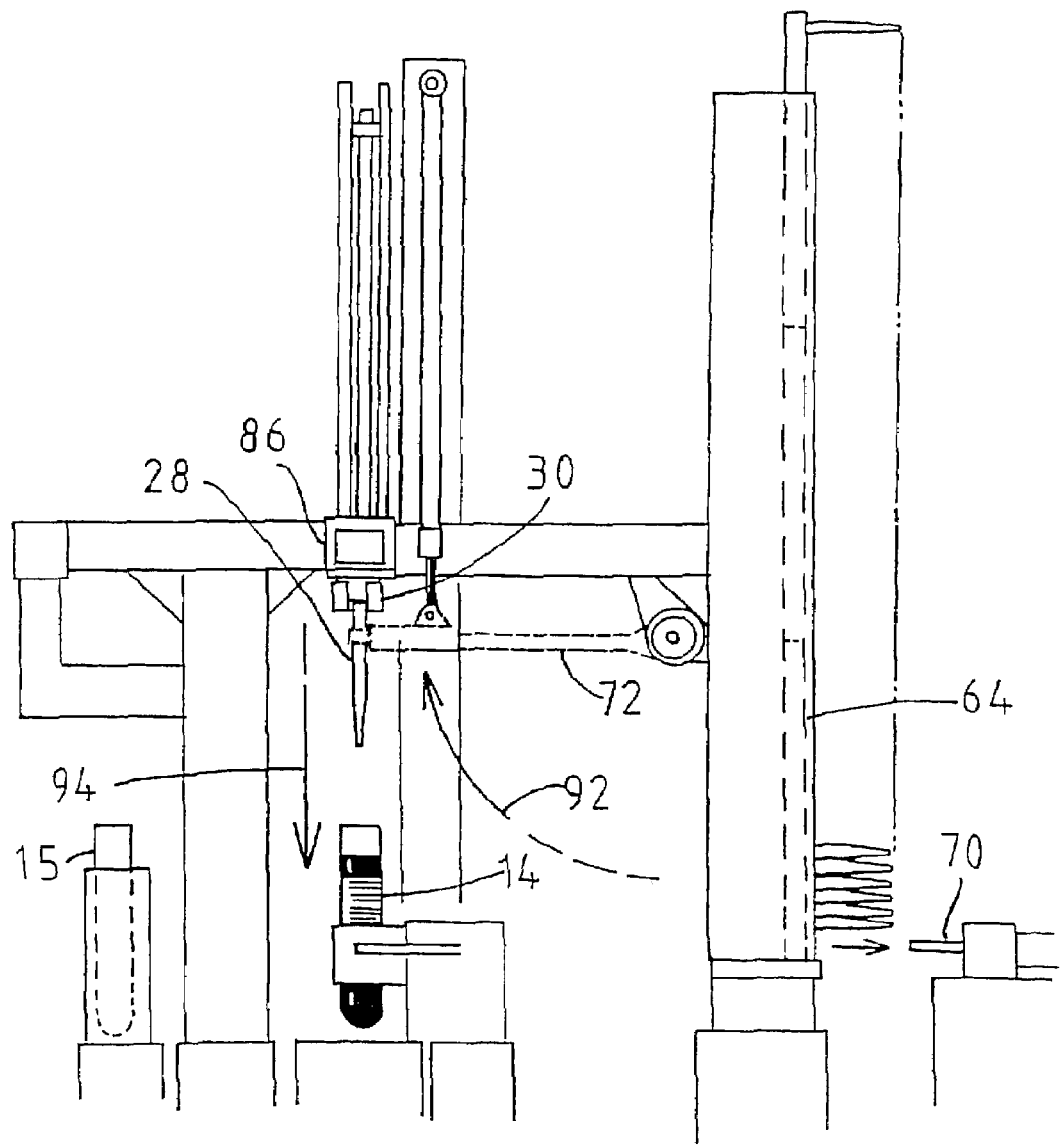

FIG. 6B shows the pipette arm 72 moving in the direction of arrow 92 and placing the pipette tip 28 onto the probe 30 of the sample aspiration and dispensing means 86. The pipette tip 28 is then lowered into the primary specimen tube 14 in the direction of arrow 94 to aspirate a sample of the specimen. At the same time the plunger 70 is withdrawn and the pipette tip holder 64 drops to the next row of pipette tips 28.

Figure 6C:
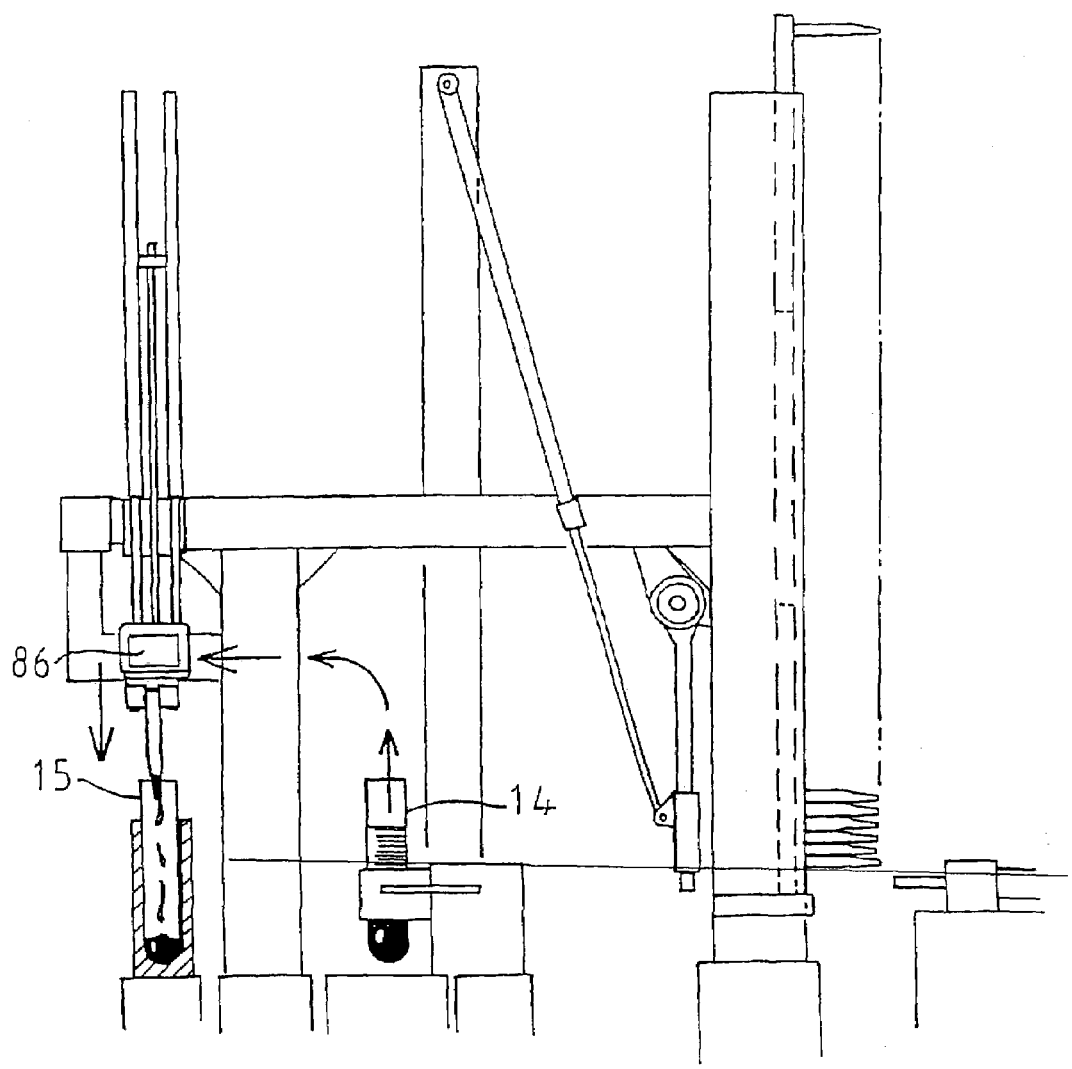
FIG. 6C shows an embodiment of the sample aspiration and dispensing means for the system according to the invention.

FIG. 6C shows the sample aspiration and dispensing means 86 dispensing a sample aspirated from the primary specimen tube 14 to a secondary sample tube 15.

Figure 6D:
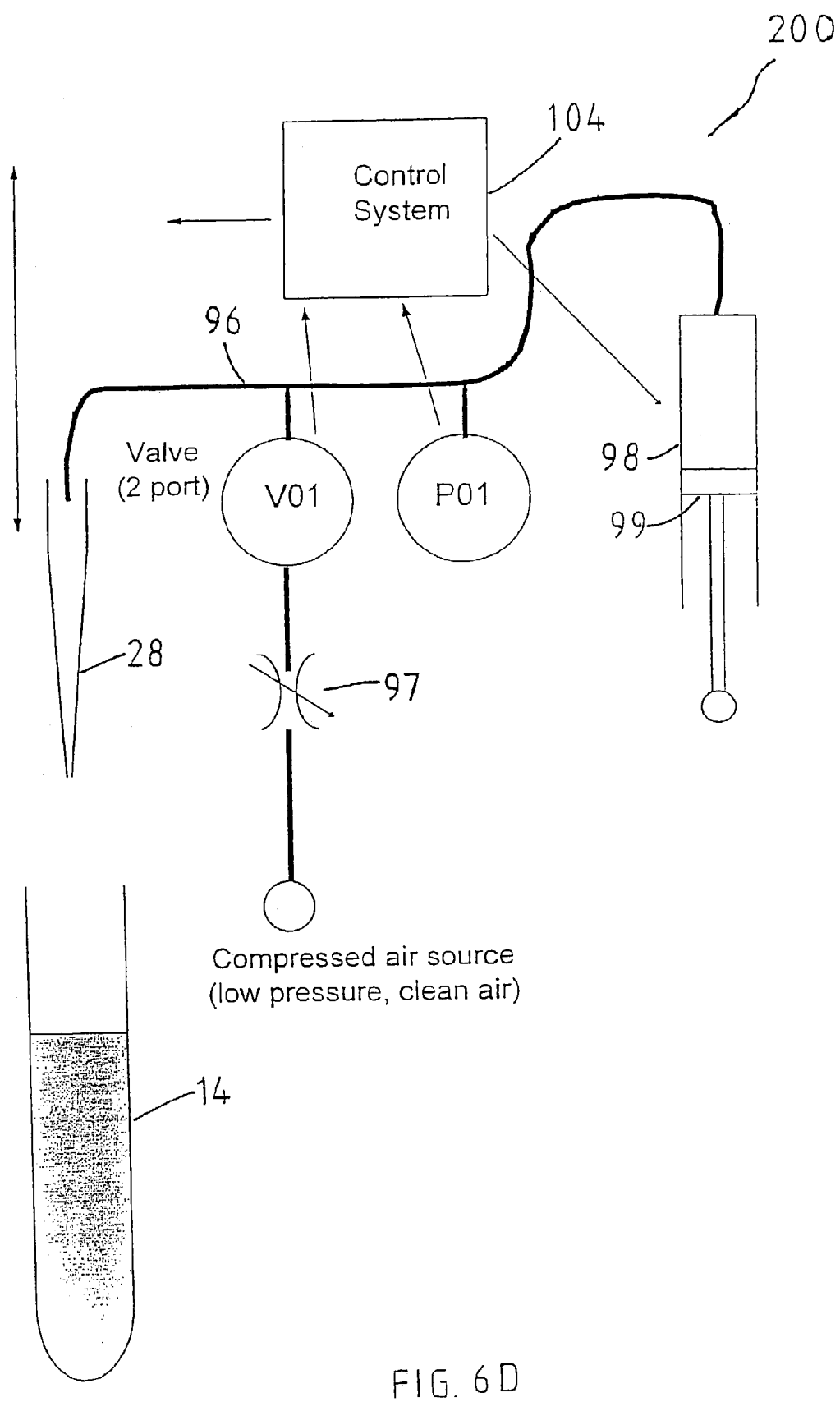
FIG. 6D is a schematic diagram showing an arrangement for sample level detection and clot detection.

Prior to the sample aspiration operation, the system 10 of the present invention is arranged to detect the level of the sample in the tube 14. FIG. 6D shows a schematic view of components in a level detection arrangement 200 for both level and clot or clog detection.

The arrangement 200 has a tubing 96 with one end connected to an automatically controlled pump which in this case is a syringe 98, and the opposite end positioned for aspirating or dispensing through a pipette tip 28. Also connected to the tubing 96 is a 2-port valve V01 which is in connection with a low pressure air source through a flow restriction 97, and a pressure sensor P01. A controller or controller system 104 which in this case is the same computer system for controlling the system 10 is arranged to control the 2-port valve and the syringe 98. The controller 104 also controls movement of the pipette tip 28 towards and away from the tubes 14, 15.

In operation the system 10 is controlled so that the tube handler 46 positions the tube 14 held therein under the raised pipette tip 28. The piston 99 in the syringe 98 is placed at its neutral or zero position as it is not used for level detection.

When the tube 14 is at that position the controller 104 opens the valve V01 for the low pressure air to enter the tubing 96 and out through the tip 28. After elapse of a predetermined time for the air pressure to stabilise the controller 104 reads the pressure at the pressure sensor P01 and stores the read pressure as the reference baseline pressure.

The controller 104 then controllably moves the tip 28 downwards in discrete steps. At each step the pressure at P01 is read and compared with the stored baseline pressure. When the pressure difference is greater than a predetermined value then the level of the sample is detected.

On detection of the level of the sample, the controller 104 closes the valve V01 and the syringe 98 is now ready for aspiration.

For aspiration, the controller 104 moves the tip 28 down slowly and at a rate with the dropping sample level. At the same time the pressure at P01 is monitored. If the pressure form P01 drops below a predetermined value then a clot or clog at the tip 28 is detected. The controller 104 immediately stops the aspiration operation and the downward movement of the tip 28. The tip 28 detected with a clot or clog is then moved to a tip ejection arrangement 400 where it can either be ejected automatically or be positioned for manual ejection.

Figure 6E:
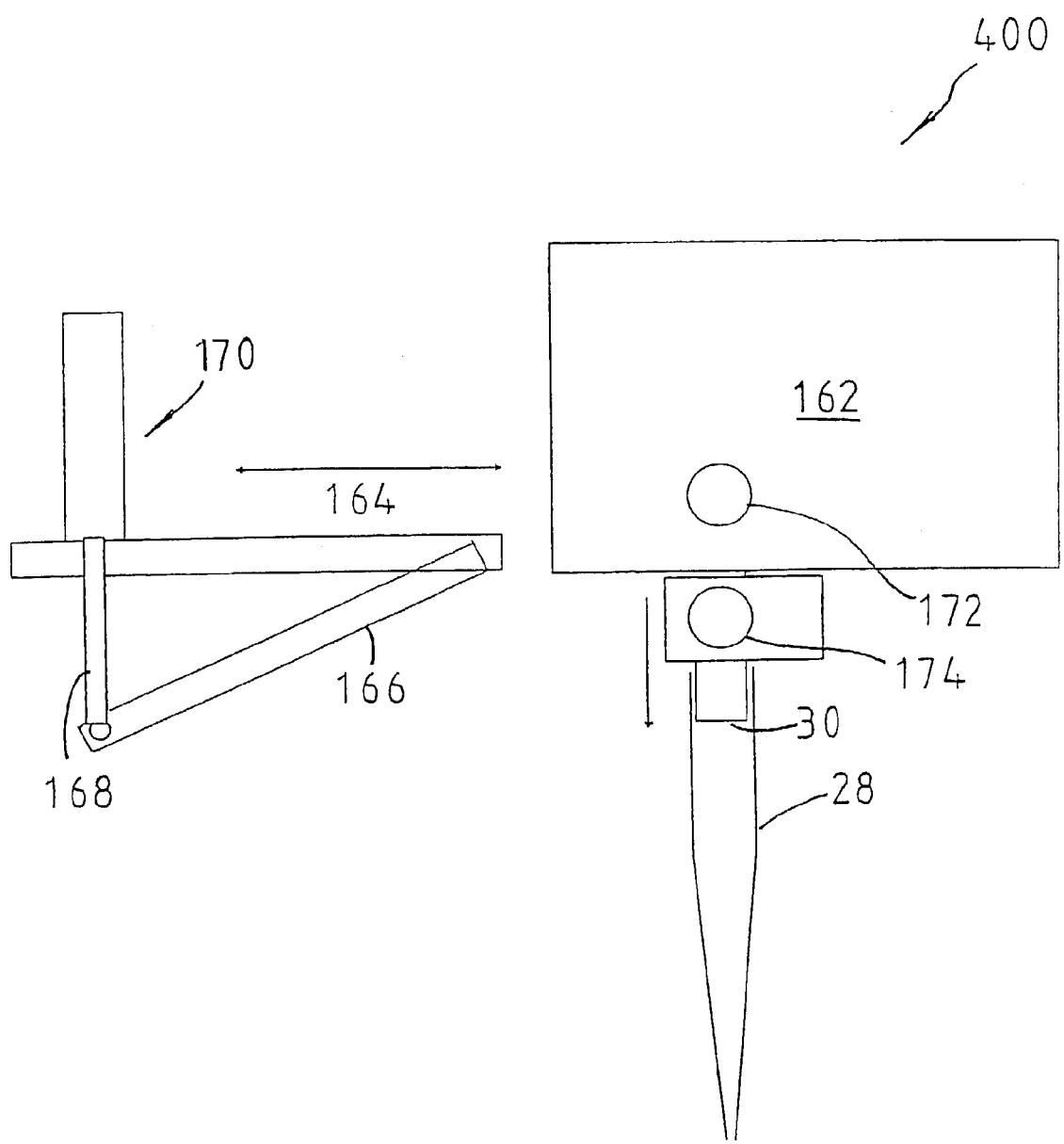
FIGS. 6E and 6F show a tip ejection arrangement for the system according to the present invention.
Figure 6F:
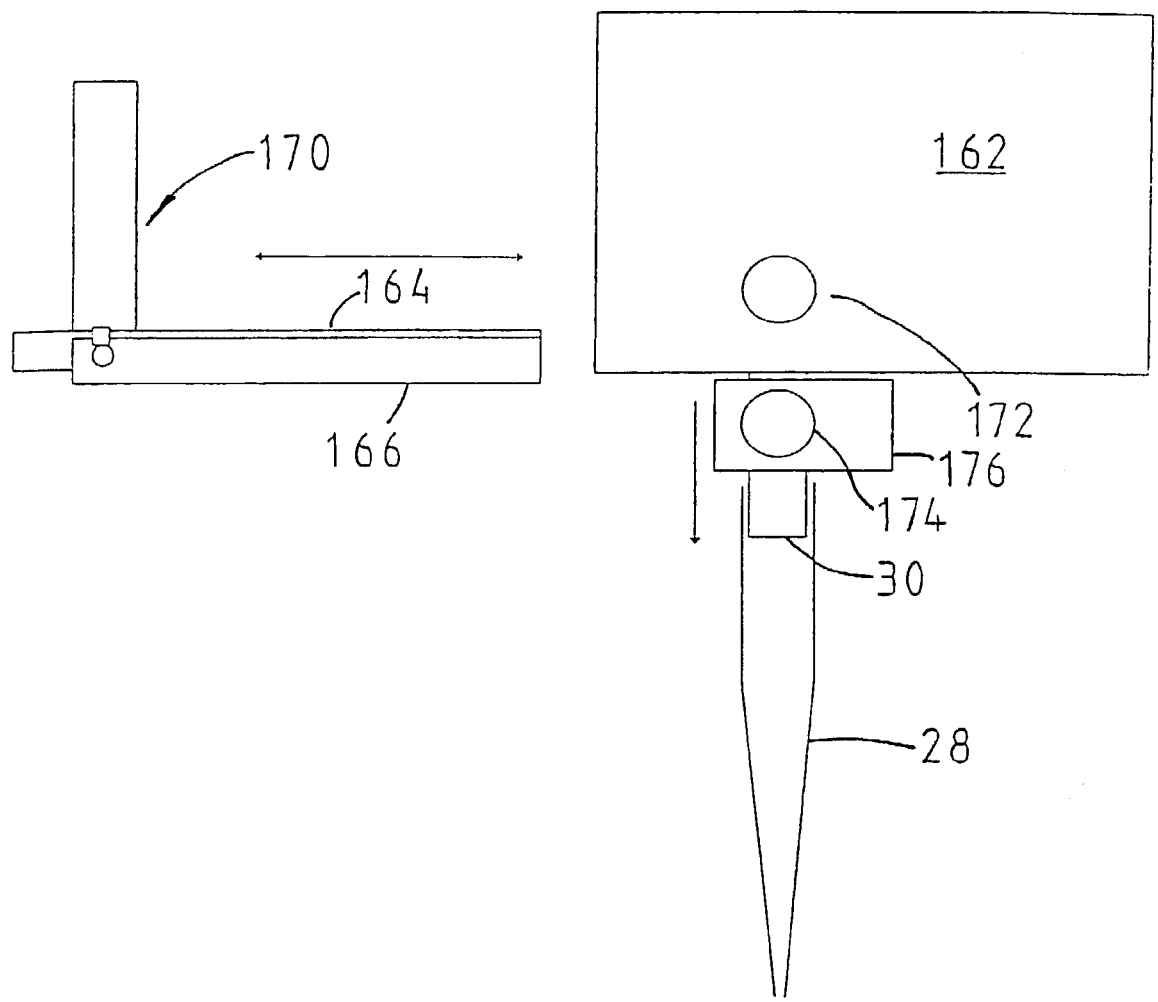

The system 10 includes a pipette tip ejection arrangement 400 as shown in FIGS. 6E and 6F. Referring to FIG. 6E, the arrangement 400 has a aliquot carriage 162 which is controlled to move towards an ejection ramp assembly comprising a horizontally arranged bar 164 and a pivotally moveable bar 166. The bar 166 is connected to the moveable rod 168 of a pneumatic actuator 170. In normal operation the rod 168 is positioned in the extended position. The rod 168 thereby placing the bar 166 to form a ramp surface.

The carriage 162 has a pair of spaced rollers 172 and 174 which are arranged to receive the bars 164 and 166. The roller 174 is fixed to a body 176 which is slidable along the probe 30 and is biased in an up position as shown.

When the sample in the tip 28 has been dispensed the controller commands the carriage 162 to move towards the ejection assembly. The bars 164 and 166, when entering the space between the two rollers 172 and 174 come into contact with the roller 172 and 174 respectively. Further movement of the carriage 162 forces the body 176 to slide downwardly along the probe 30 and at the same time the body 176 pushes the tip 28 away from the probe 30 for ejection.

When a clot or clog in the tip is detected, the controller commands the actuator 170 to retract, the rod 168 as shown in FIG. 6F. In this position the bars 164 and 166 can enter the space between the rollers 172 and 174 freely, without causing ejection of the tip 28. The sample in this tip 28 can therefore be recovered by manually switching the actuator to extend the rod 168.

Figure 7A:
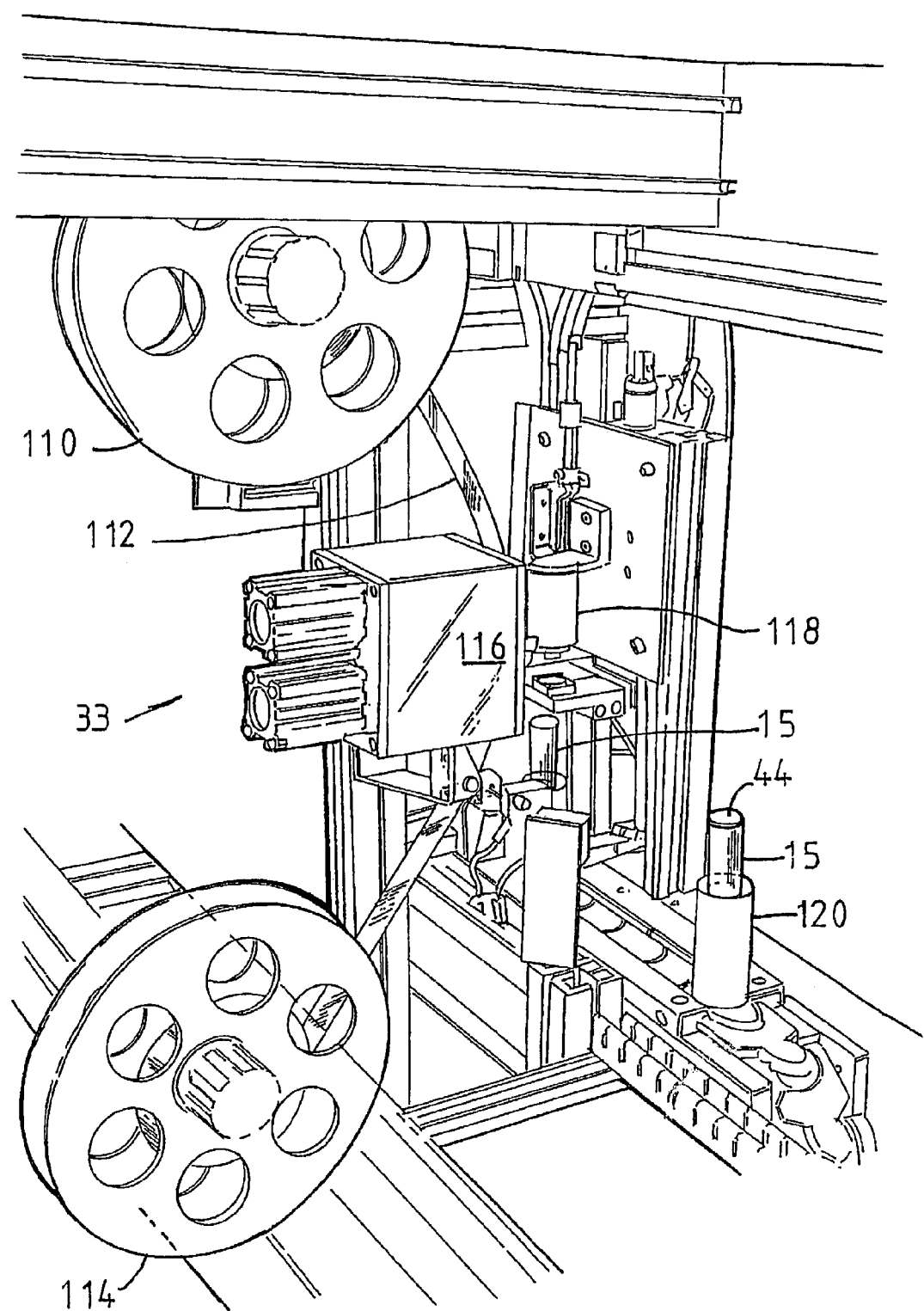
FIG. 7A shows an embodiment of the secondary sample tube capping apparatus for the system according to the invention.

FIG. 7A shows the secondary sample tube capping apparatus 33 which comprises a reel 110 holding laminate tape 112 and a take up reel 114 for the tape 112 which has been used. The tape 112 passes through a punch and die assembly 116 which punches caps 44 (see FIG. 7) The caps 44 are placed over the open ends of the secondary sample tubes 15 and each laminate cap 44 is heated by the heater assembly 118 which results in the laminate cap 44 being sealed over the top of the secondary sample tubes 15. The secondary sample tubes 15 are held in holders 120 attached to a conveyer belt (see FIG. 9).

Figure 7B:
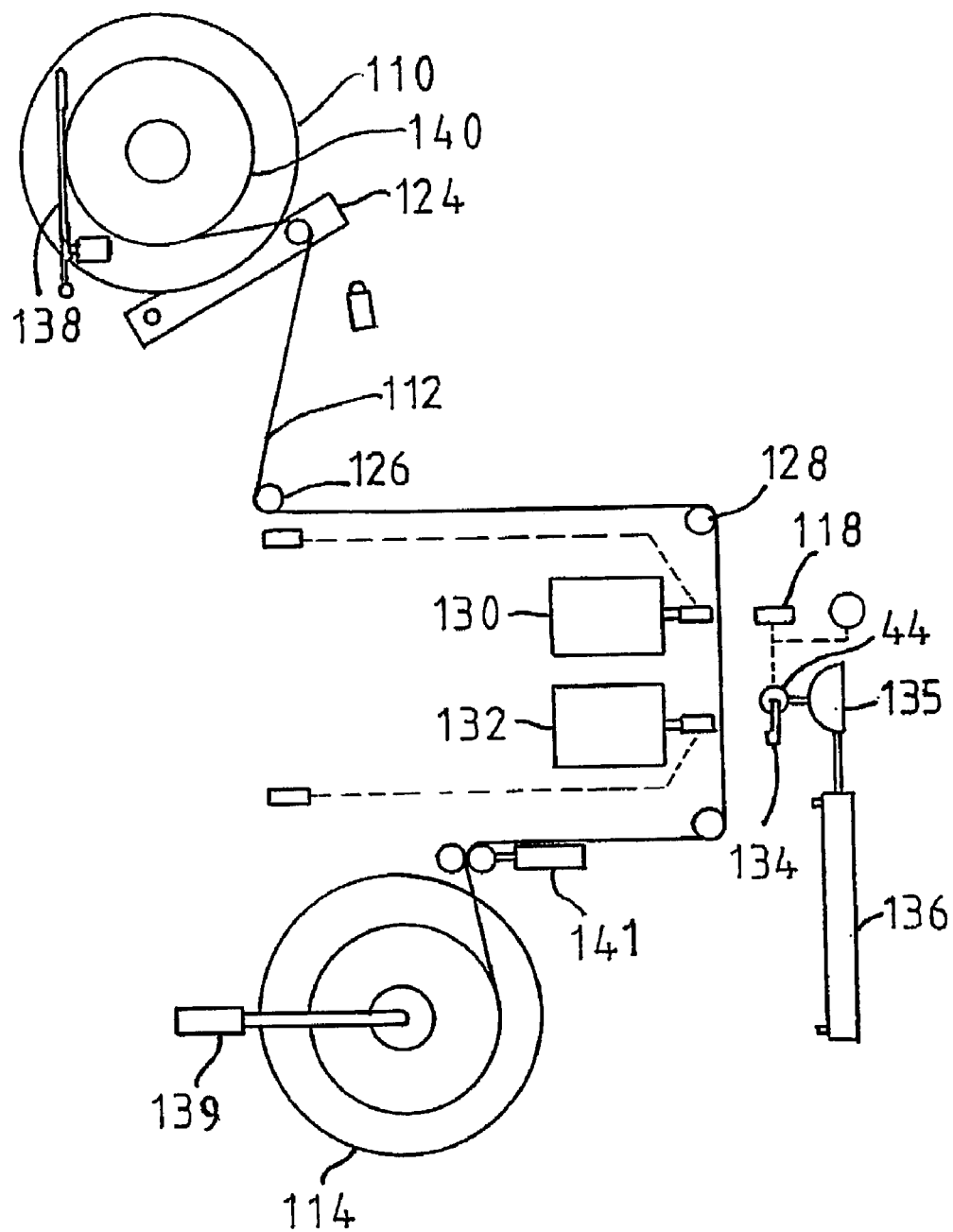
FIG. 7B shows a schematic plan view of the apparatus of FIG. 7A.

FIG. 7B shows a schematic plan view of the apparatus 33 of FIG. 7A. Reel 110 holding laminate tape 112 is passed over a spring loaded tensioner 124 which allows the tape 112 to be dispensed without accelerating the reel 110 as it passes onto rollers 126, 128. The tape 110 passes pneumatic cylinder punches 130, 132 which selectively punch out the caps 44 of different diameters for the secondary sample tubes 15 which may have openings of different sizes (not shown). The punched out caps 44 are held by a vacuum line (not shown) and moved by a transport device 134 to be placed over the tops of the secondary sample tubes 15 (not shown) wherein they are affixed using a heater assembly 118. A rotatary actuator 135 is provided to swing the caps 44 around for heat sealing by the heater assembly 118. A pneumatic actuator 136 is selectively controlled to move to one of the punches 130, 132 from which a cap is to be removed. Low supplies of the tape 112 are detected by the indicator 138 in contact with the spool of tape 140. The take up reel 114 is rotated by a motor 139 and is associated with an indexing motor 141 to move the tape 112 the correct distance pass the pneumatic cylinder punches 130, 132.

Figure 8A:
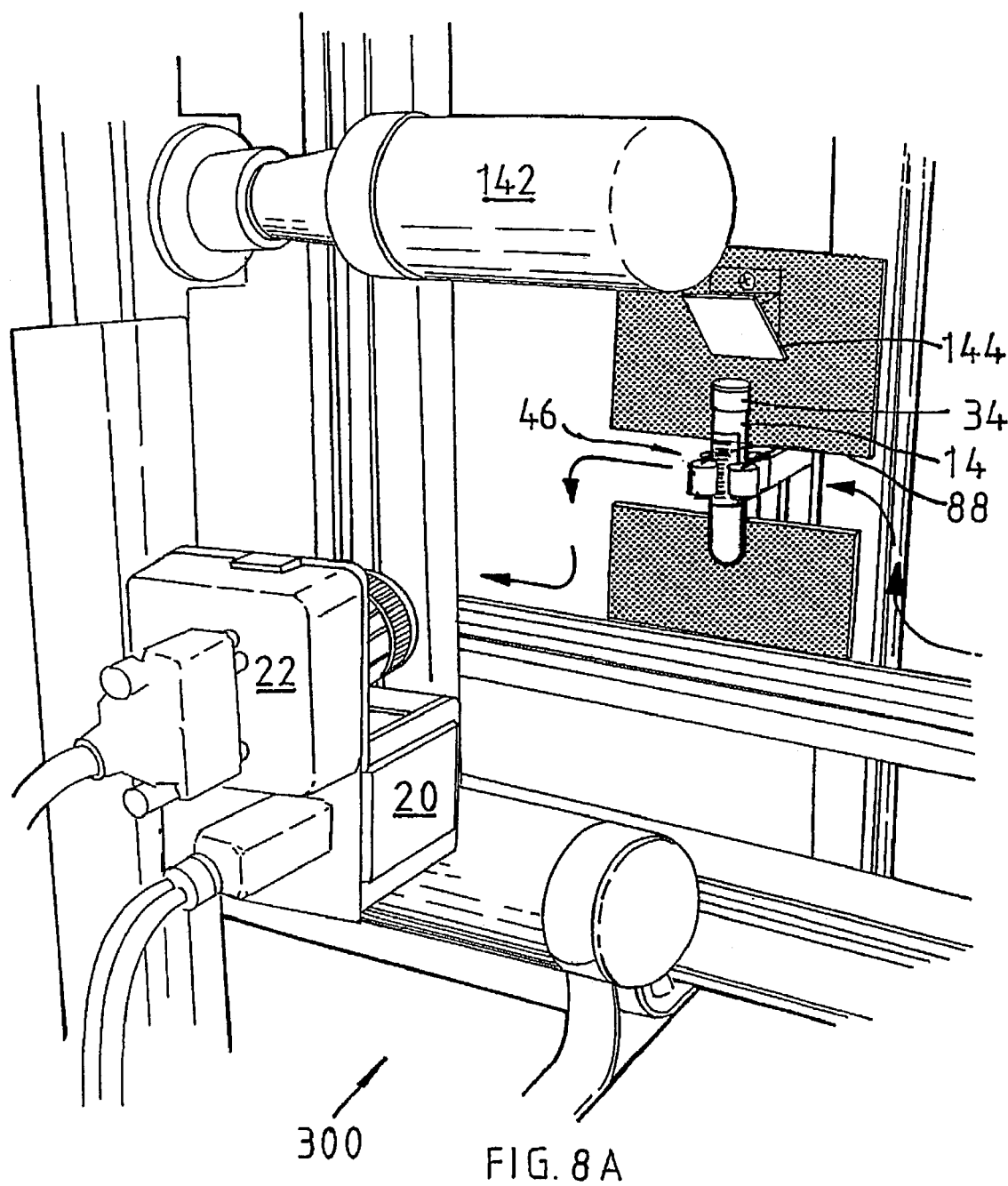
FIG. 8A shows a perspective view of an embodiment of the image analyser for the system according to the invention.

FIG. 8A shows a perspective view of an image analysing apparatus 300 comprising a digital camera 22 and a bar code reader 20. Light from a fluorescent bulb 142 is shone on the primary specimen tube 14 and the digital camera 22 captures the shape of the tube 14 and the colour of the cap 34 reflected by a mirror 144, and the bar code reader 20 reads the bar code label 88 on the tube 14. The mirror 144 is used to view the colour of the top of the cap 34 on the tube 14 only. This allows the system to positively identify tubes 14 which have two colours on the top of the cap. The digital camera 22 also captures the dimensions of the tube 14 and the depth of the layer of the specimen to the analysed, amongst a number of layers of the specimens in the tube 14. In order that the specimen is correctly captured by the digital camera 22, a controller (not shown), upon receiving a signal from the reader 20, rotates a pair of grippers of the tube handler 46 (see FIG. 1) holding the tube 14 by a predetermined angle so that the camera 22 can capture images of the sample through a portion or window of the tube 14 not obscured by the label 88 and the tube manufacture's label (not shown).

Figure 8B:
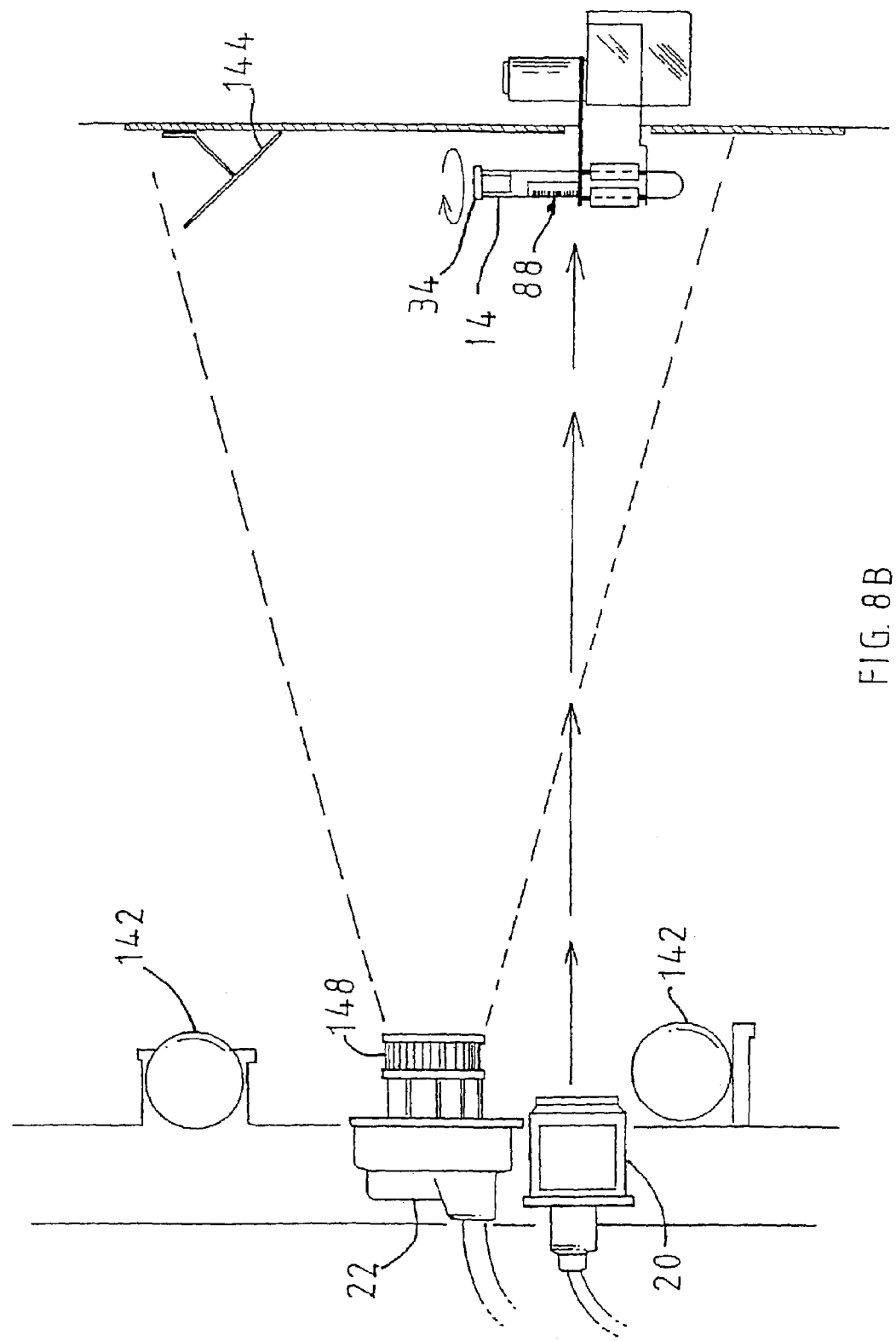
FIG. 8B shows a side elevation of the image analyser of FIG. 8A.

FIG. 8B is a side elevation of the image analyser 300 of FIG. 8A. The image of the tube 14 reflected by the mirror 144 is captured by the lens 148 of the digital camera 22 which also records the colour or colours of the cap 34. The bar code label 88 on the tube 14 is read by the bar code reader 20. Illumination for imagining the tube 14 is provided by fluorescent lamps 142.

In this embodiment, a number of windows within the field of view of the camera 22 are defined for capturing images of parts of the tube 14. In addition a pair of windows are defined for capturing respective contrasting black and white colour patches arranged in fixed positions in front of the camera 22.

The captured images of the contrasting colour patches are used to calibrate a bias due to variation in brightness of the light 142. The bias is calibrated in this embodiment by comparing the brightness level between captured images of the colour patches and that stored in memory of a computer of the controller.

Following adjustment of the calibrated bias the captured images through said plurality of windows are compared to stored images of corresponding windows, using an algorithm.

For the tube identification and liquid level detection the controller is programmed to image predefined windows and maximum tolerance of differential as follows:
1. Define the coordinates of sub-image area used for tube identification;
2. Define the coordinates of black colour calibration patch;
3. Define the coordinates of white colour calibration patch;
4. Define the coordinates of cap top view (via mirror) (ref.A1)
5. Define the coordinates of cap profile (must include cap profile regardless of tube length.) (ref.A2)
6. Define the maximum image difference tolerance (ref.MD); and
7. Define the coordinates of sub-image area used for liquid level detection.

Information for each type of tubes 14, 15 is obtained by the following procedure:

1. Place tube in front of camera;
2. Take picture of full field view with 24 bit RGB colour depth;
3. Create sub-images of areas used for tube identification (top view of cap via mirror and profile view including the cap and at least 1 cm of tube body of the smallest tube, and the black and white colour calibration areas.)
4. Enter a unique tube identifier text in TID;
5. Enter relevant physical attributes or characteristics of tube (diameter, length, max volume, cap type . . . );
6. Enter gel/no gel attribute;
7. Enter specimen type associated with this tube; and
8. Save sub-images and data to storage media.

To minimise error readings due to variations in light level a biasing factor is first determined by calculating the average value of the white and the black colour calibrations areas and save it in memory. The information saved in the storage media is loaded in RAM memory prior to imaging an incoming tube by:
1. Place the tube in front of the camera with the gap level facing the camera;
2. Take picture of full field view with 24 bit RGB colour depth;
3. Create sub-images of areas used for tube identification (top view of cap via mirror and profile view including the cap and at least 1 cm of tube of the smallest tube, and the black and a white colour calibration areas);
4. Calculate the average value (using Pixel values) of the white and the black colour calibration area and save it in memory;
5. Process the current sub-image against all calibrated tubes in the following way:
    Create a look-up table for RGB values using the average values from the black/white colour calibration of the current image and reference images. (ref. LUT)
    Subtract A1 of current image from A1 of reference using LUT and store value as D1;
    Subtract A2 of current image from A2 of reference image using LUT and store value as D2;
    Add D1 and D2 and save as total difference in DT; and
    If current DT is the smallest DT of the run then save this DT as DS and store the tube id in TID.
6. If DS is smaller than the MD then a valid tube is identified;
7. Use TID to find the physical parameters of the tube and the associated specimen tube.

For detection of the sample level of the identified tube the following steps are followed:
1. Create sub-images or areas used for liquid level detection (centre part of tube about 50 pixels wide and full length to tube profile). Exclude top view via mirror;
2. Blank out unused areas (cap area, bottom radius) using the physical properties of the tube;
3. Run a laplace filter through all pixel columns of all colours of the sub-images and store result in memory;
4. Find edges in laplace results and store result in memory;
5. Combine the edges of RCB into one edge value array;
6. Filter edge value array using a block filter;
7. Validate the remaining edges against the physical properties of the tube;
8. Validate the remaining edges against max. and min. volume parameters of the tube;
9. Validate the remaining edges against the gel/no gel parameter of the tube; and
10. Use the remaining edges as top liquid level and bottom liquid level.

The type of tube 14 being viewed is identified when matching images are found or when images within a predetermined threshold of matching are found. Any of the tubes 14 not meeting one of these conditions are rejected and returned to the loading station.

This system effectively combines characteristics of the tube 14 for identifying the type of tube 14 before the camera 22. The characteristics include cap colour, cap shape and overall tube dimensions.

Along with information in the windows for capturing characteristics of each type of tubes 14, in the memory are also stored information relating to corresponding brand, type, volume, gel content etc. Therefore when a match or close match is determined, the computer can identify the type of tube 14 and the volume of the plasma or serum available in the sample tube 14.

Figure 9A:
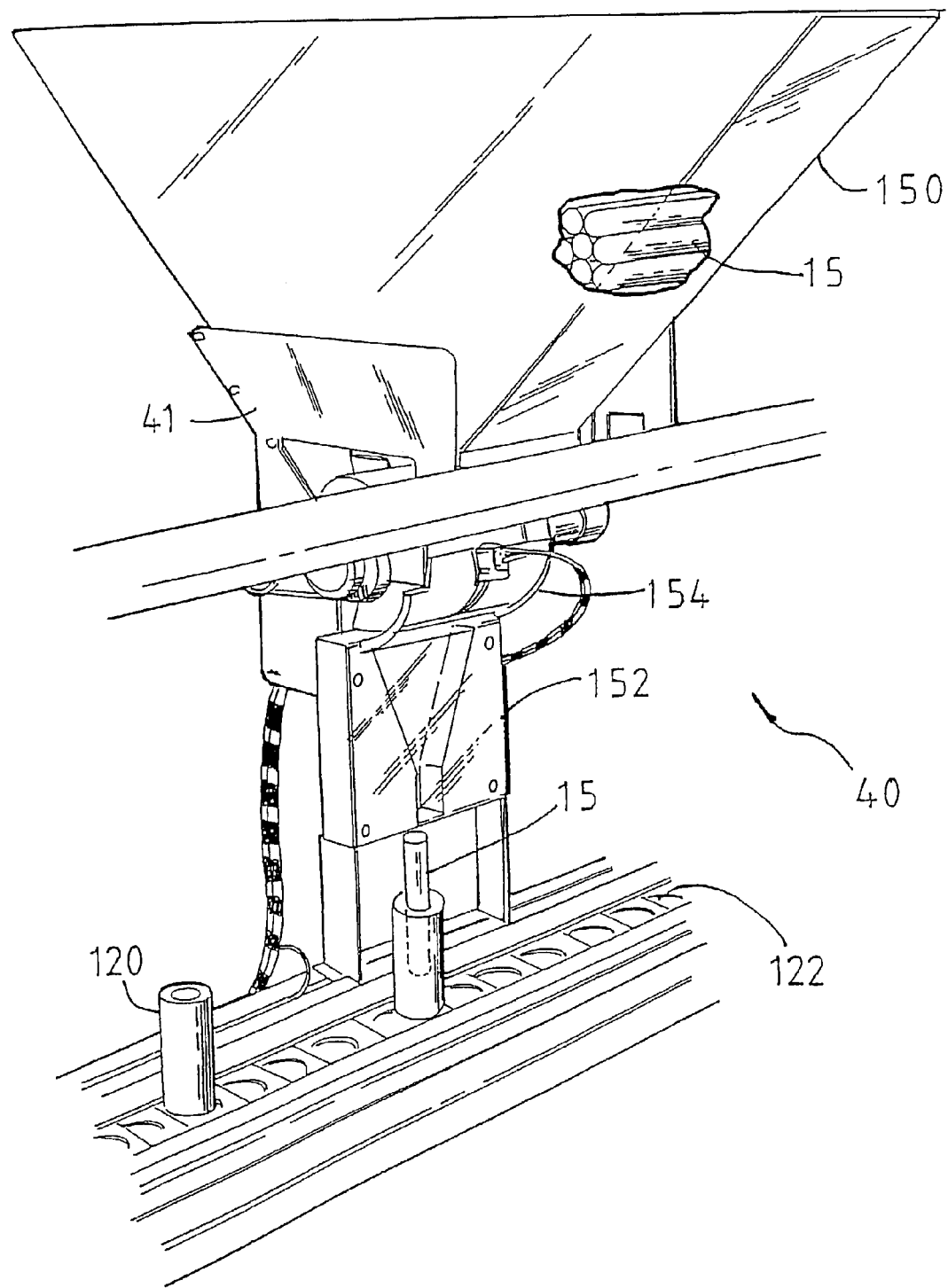
FIG. 9A shows an embodiment of the hopper means for the system according to the invention.

FIG. 9A shows the hopper means 40 wherein horizontally aligned secondary sample tubes 15 packaged in a triangular shaped container 150 may be loaded into the upper portion 41 of the hopper 40. A Y shaped guide 152 causes the sample tubes 15 to fall in the correct vertical position into holders 120 on a conveyer belt 122. Although not shown in detail the secondary sample tubes 15 are delivered to a rotary magazine 154 prior to release into the guide 152.

Figure 9B:
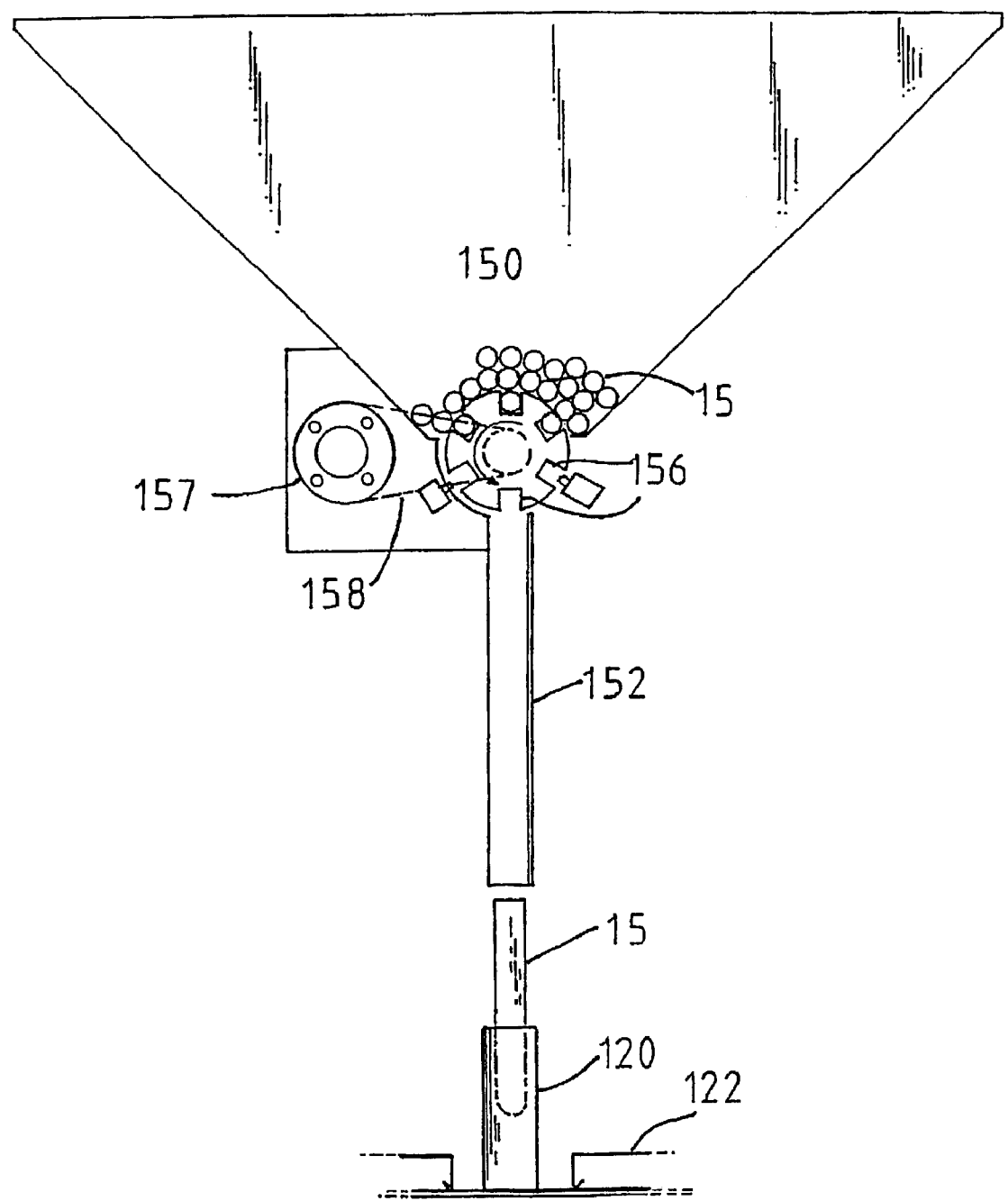
FIG. 9B shows an elevation of the hopper means of FIG. 9A.

FIG. 9B shows an elevation of the hopper means 40 of FIG. 9A wherein the secondary sample tubes 15 from the container 150 are loaded into circumferentially located compartments 156 of the rotary magazine 154. The magazine 154 is rotated by a motor 157 with a drive belt assembly 158 and the secondary sample tubes 15 are allowed to fall into the guide 152 and into the holders 120 of the conveyer belt 122.

Figure 9C:
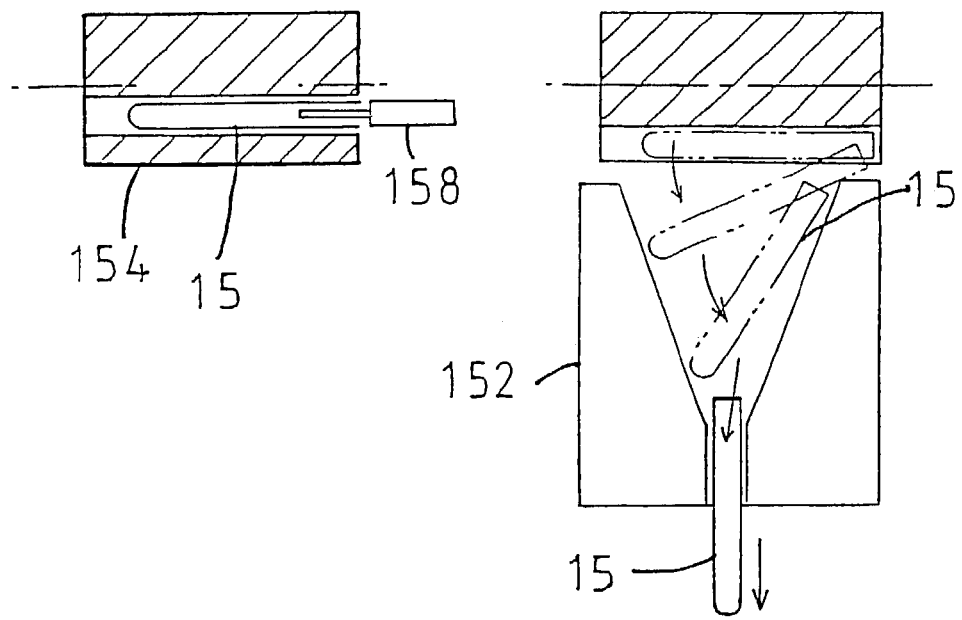
FIGS. 9C and 9D show the operation of the sideways plunger of the hopper means of FIG. 9A.

FIG. 9C shows the sideways plunger 158 in co-operation with the rotary magazine 154. When the plunger 158 is not in contact with a closed end of a secondary sample tube 15 it does not displace the tube 15 and the tube 15 falls into the guide 152 in the correct vertical position.

Figure 9D:
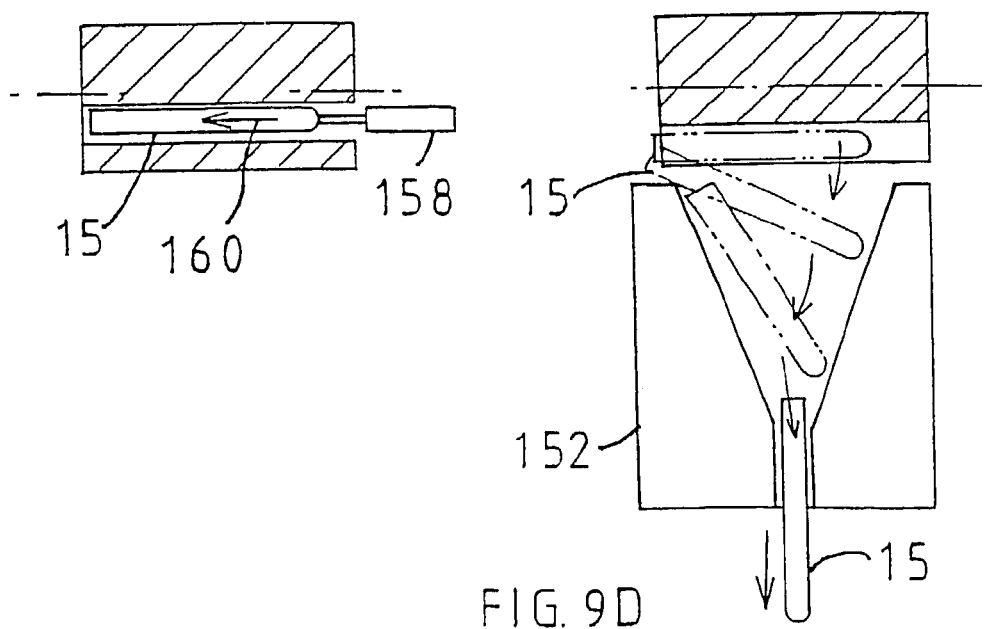

FIG. 9D shows the sideways plunger 112 when in contact with a closed end of a secondary sample tube 15 causes the tube 15 to be displaced in the direction of the arrow 160 resulting in the displaced tube 15 falling into the guide 152 in the correct vertical position.

Figure 10:
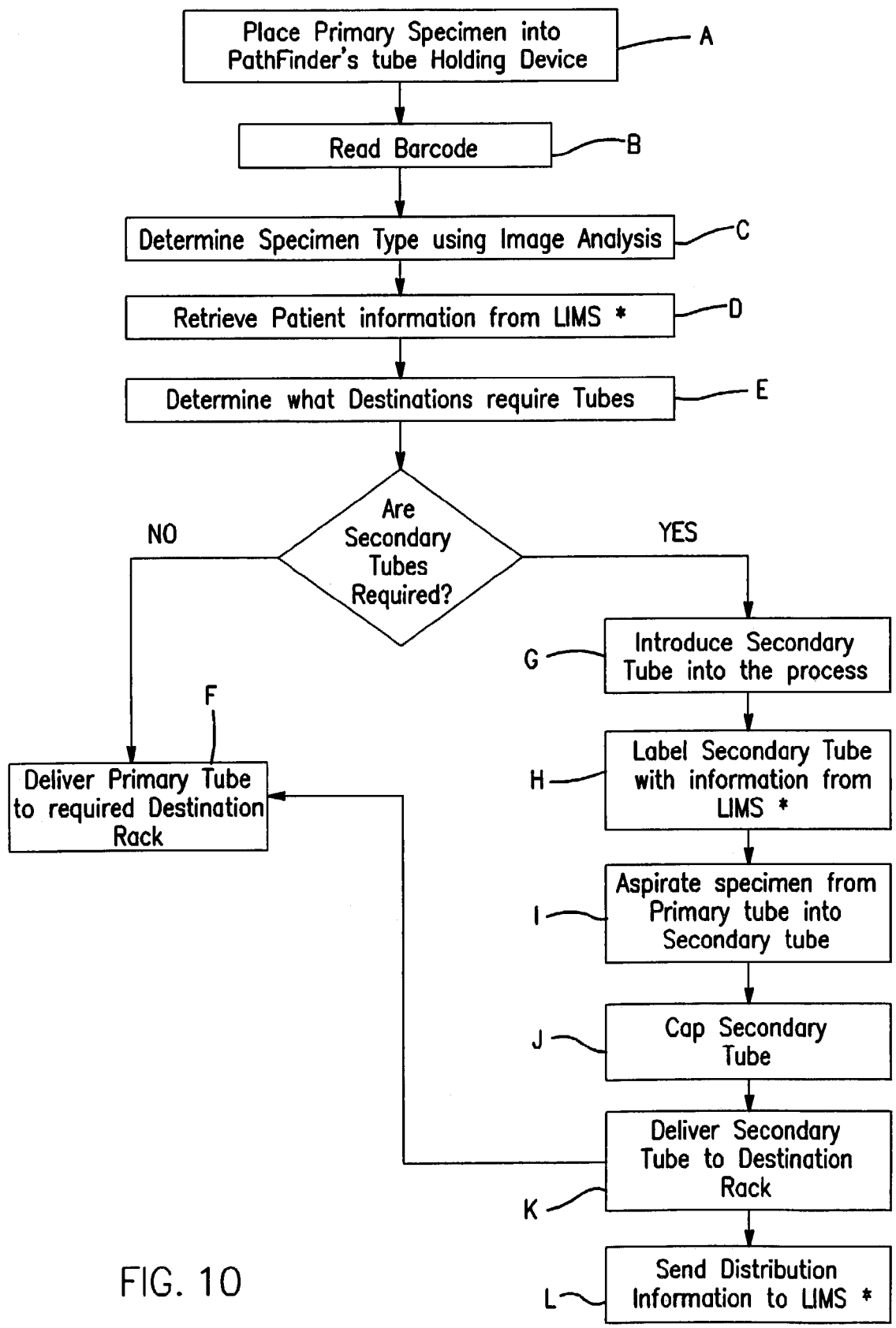
FIG. 10 is a flow chart showing the basic operations of the computerised laboratory information management system according to the invention.
Figure 11:
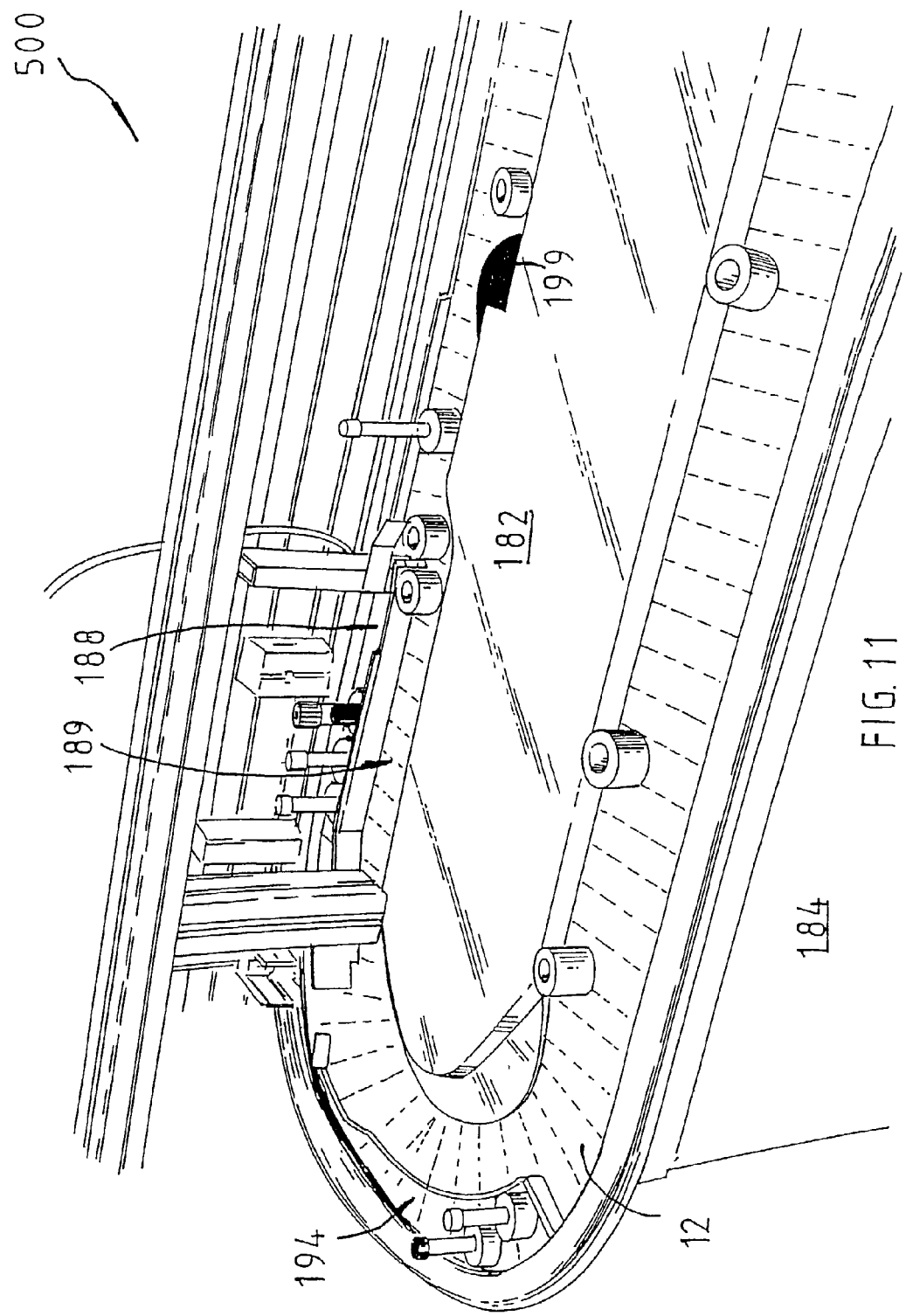
FIG. 11 shows a partial perspective view of a sample tube loading station for the system according to the present invention.

FIG. 10 shows a flow chart of the computerised laboratory information management system 10, referred to as LIMS in the flow chart, according to the invention. A primary specimen tube 14 containing a specimen is introduced to the system 10 by placing it in a tube holding device (step A) also referred to as the presented tube handler in the description of FIG. 1. The bar code 88 on the primary specimen tube 14 is read by a bar code reader 20 (step B). The specimen tube type and level of specimen in the tube 14 is determined by the image analyser 22 as hereinabove described (step C). Patient information stored on the computerised laboratory information management system is retrieved (step D) to determine what destinations or rack stations 38 associated with the specimen require tubes 14 (step E). If no secondary sample tubes 15 are required the primary specimen tube 14 is delivered to a particular destination or rack in the work station area 38 of the robotic arm as previously described (step F). If secondary sample tubes 15 are required, secondary sample tubes are introduced into the system 10 (step G) wherein they are label led with information retrieved from the computerised laboratory information management system (step H). The secondary sample tubes 15 are then filled with samples aspirated from the primary specimen tube 14 (step I) and the secondary sample tubes 15 are then automatically capped (step J). The capped secondary sample tubes 15 are then transferred to racks which are also placed in the work station 38 of the robotic arm as previously described (step K). Information concerning the placement of tubes 14, 15 in specific destination racks is also sent to the computerised laboratory information management system (step L).

Referring to FIGS. 11 to 17 there is shown a sample tube loading station 500 for the system 10 (partial view only) according to the present invention. The station 500 has an articulated tube conveyor 12 which loops around a holding area 182 and is positioned on a support 184.

The conveyor 12 has a barrier 186 dividing a section of the conveyor 12 into a buffer zone 188 for receiving carriers or pucks 190 with tubes 14 positioned thereon and a by-pass passage 189. The tubes 14 in the buffer zone 188 are for loading onto the tube handling station 16 by the tube handler 46 (see FIG. 2).

Figure 12:
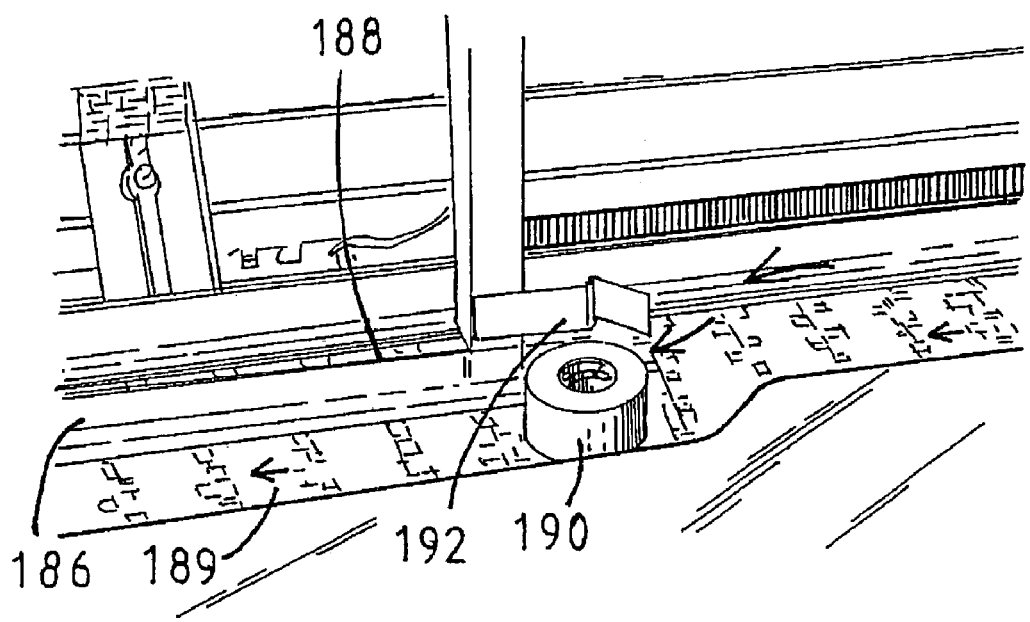
FIGS. 12 to 15 show views of different situations at a buffer zone of a conveyor arrangement for the loading station shown in FIG. 11.
Figure 13:
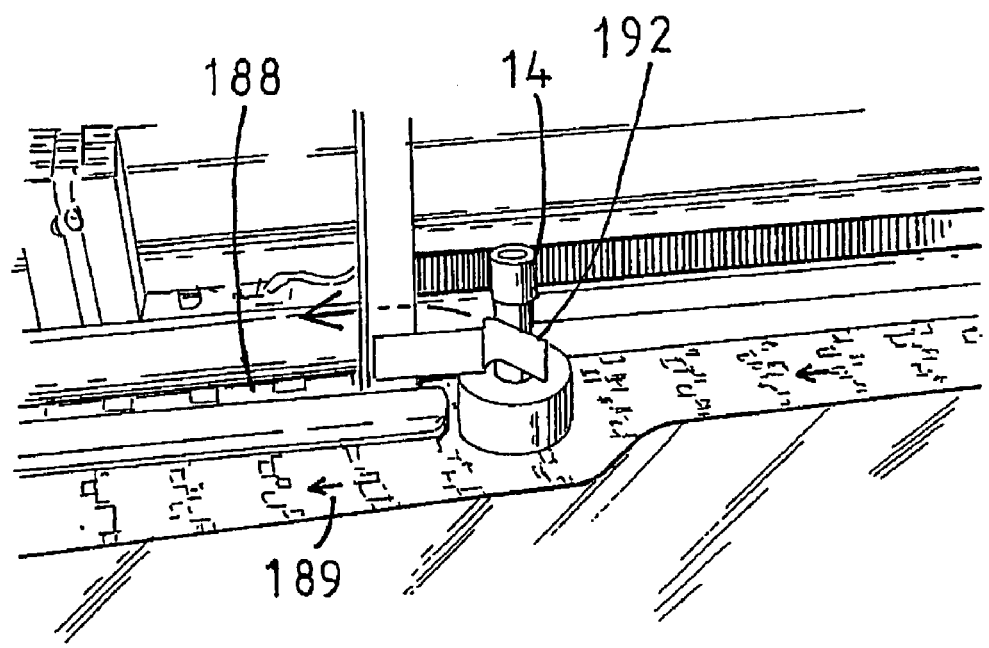
Figure 14:
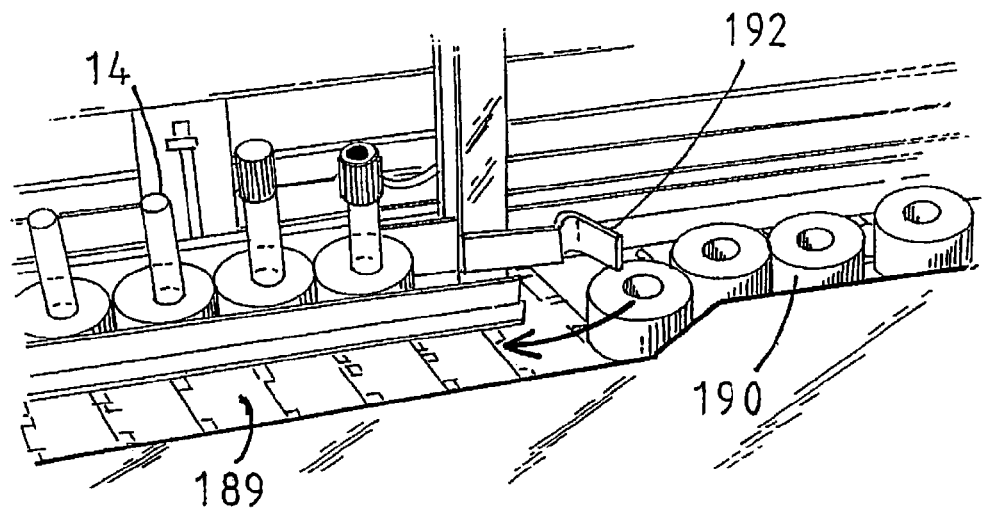

As shown clearly in FIGS. 12 to 15, a diversion bar 192 positioned at the entrance of the buffer zone 188 and just above emptied pucks 190 allows the empty pucks 190 to move into the by-pass passage 189 (see FIGS. 12 and 14). The pucks 190 with tubes 14 therein are diverted or guided into the buffer zone 188 due to contact of the tubes 14 with the diversion bar 192 (see FIGS. 13 and 14).

Figure 15:
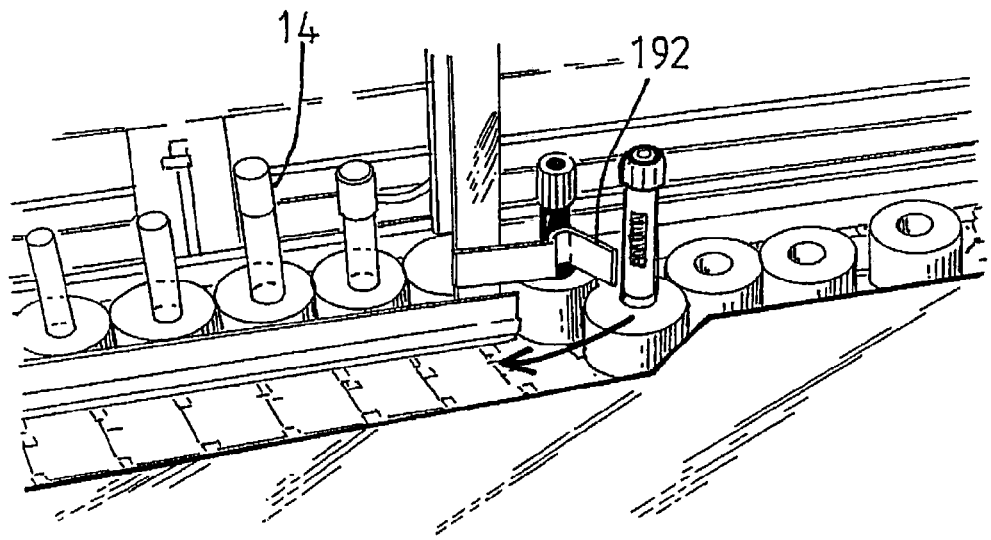

When the buffer zone 188 is full empty pucks 190 as well as pucks 190 loaded with tubes 14 move only into the by-pass 189 as shown in FIG. 15.

Referring again to FIG. 11, the conveyor 12 also has a tube reject zone 194 for receiving the tubes 14 that have been rejected by the tube handling station 16.

Figure 16:
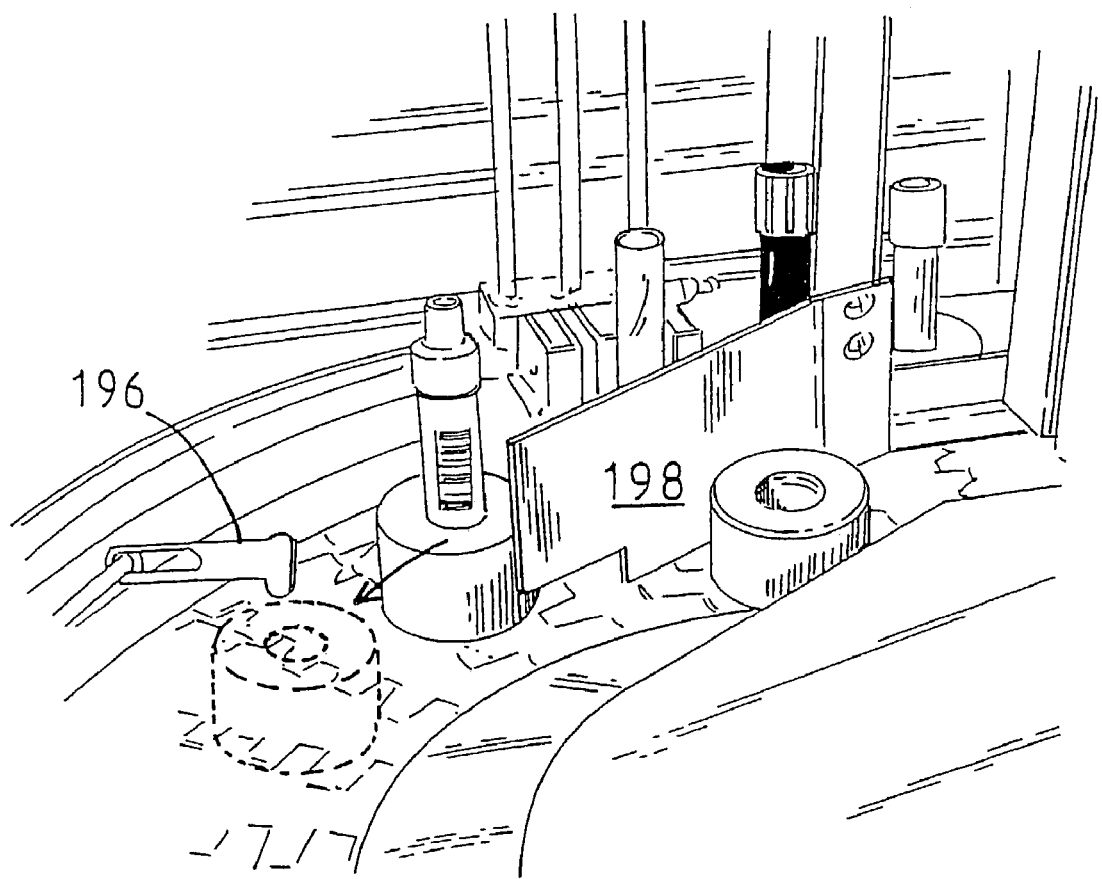
FIG. 16 shows details at the entrance of a tube reject zone of the conveyor arrangement for the loading station shown in FIG. 11.

When the system 10 detects that the presented tube 14 is not a recognised tube type or the bar code is not readable or otherwise defective, the handler 46 returns the tube 14 to the puck 190. A pneumatic actuated pin (not shown) is then actuated to push the puck 190 with the defective tube 14 out of a self-closing gate (not shown). The rejected tube 14 as shown in FIG. 16 is then diverted into the reject zone 194 by way of another diversion bar 196 positioned at the entrance of the zone 194. As for the bar 192, the bar 196 is also positioned to allow empty pucks 190 to move into the by-pass passage 189 which extends to bordering the reject zone 194. A partition 198 is fixed in position before the reject zone 194 in order to prevent other loaded pucks from entering the reject zone 194.

The pneumatically actuated pin is also employed to push the pucks 190 in the buffer zone 188 out through the gate once the system 10 determines that the tubes 14 from these pucks 190 are to proceed forward.

Figure 17:
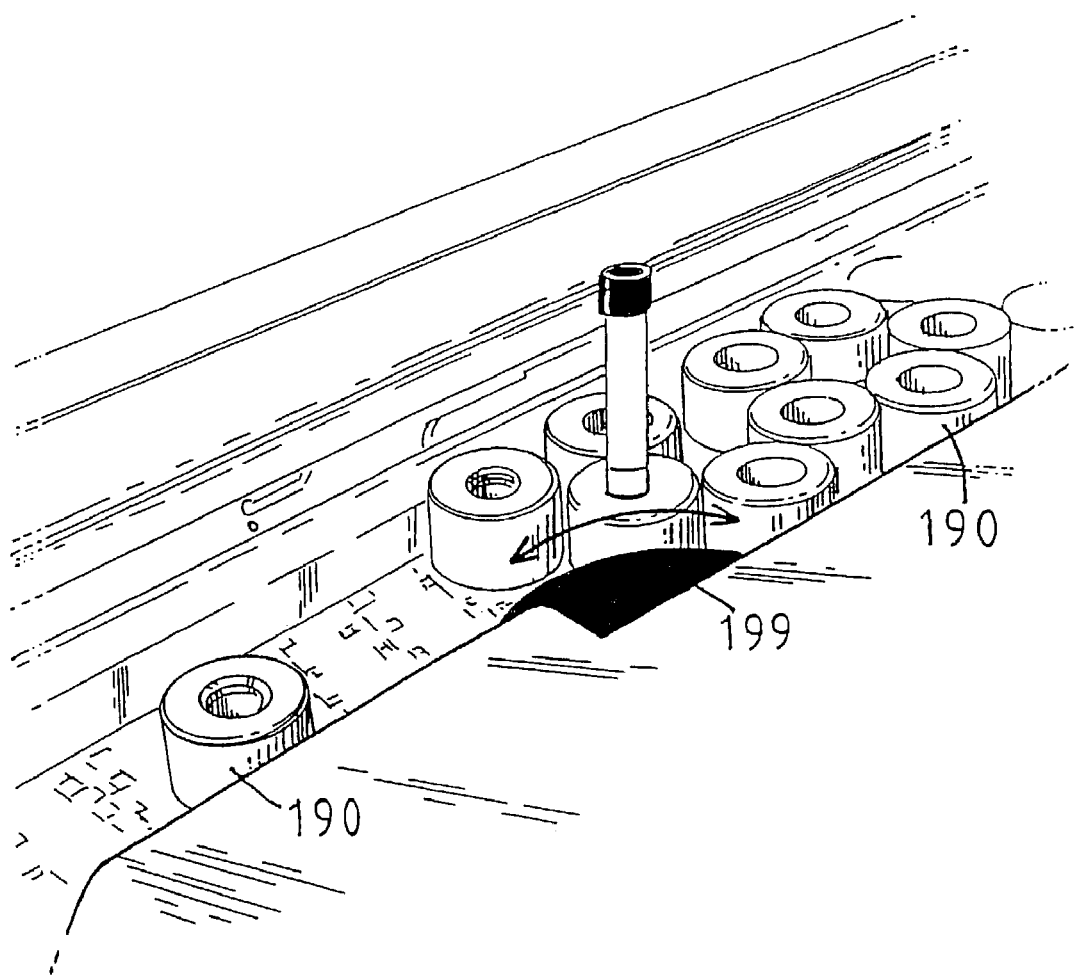
FIG. 17 shows an anti-jamming arrangement for preventing jamming on the conveyor arrangement.

Shown more clearly in FIG. 17 is an oscillating disc 199 which forces the pucks 190 to move on and thereby preventing the pucks 190 from jamming on the conveyor 180.

Whilst the above has been given by way of illustrative example of the present invention many variations and modifications thereto will be apparent to those skilled in the art without departing from the broad ambit and scope of the invention as herein set forth.

The invention claimed is:

1. A sample container handling apparatus for a pathology sample distribution system having a plurality of containers and the containers each being arranged to contain a sample for pathology analysis, the apparatus including container sealing means for sealing each of said containers with samples dispensed therein, the container sealing means having a source of heat sensitive lamination tape, means for punching the tape to form a cap seal for each said container, said punching means having a set of punches of different diameters and a punch actuator being controllably movable to actuate any of the punches for punching cap seals of a selected diameter, means for placing said cap seal over a top of each said container and means for heating the cap seal over the top of each said container to cause the cap seal to seal each said container.

2. The apparatus according to claim 1 wherein the container sealing means has a rotatable pay out reel around which the source of heat sensitive tape is wound and the tape is transferred along a tape travel path to a rotatable take up reel for receiving the tape with cap seals punched therefrom.

3. The apparatus according to claim 2 wherein the container sealing means further has a tape tensioner arranged to apply tension to the tape for controlling acceleration of the tape along the tape travel path.

4. The apparatus according to claim 1 wherein said means for placing has having a vacuum line adapted to hold the punched out cap seal and a transport device adapted to controllably place the vacuum line so that the cap seal is positioned over the top of each said container.

5. The apparatus according to claim 1 wherein a rotatable actuator is arranged to rotate the cap seal for heat scaling by the heating means.

6. The apparatus according to claim 2 wherein a low tape supply detector is associated with the pay out reel for providing an indication when the tape around the pay out reel is low.

7. The apparatus according to claim 2 wherein a motor is arranged to rotate the take up reel, and the motor is associated with an indexing means for controlling the motor to move the tape at an indexed distance along the travel path.

8. The apparatus according to claim 1 wherein the plurality of containers are of different types and the apparatus further includes a container handling station arranged for receiving the containers in turn, the handling station including a container identification means for obtaining one or more characteristics of a container presented for identification and identifying the container type by comparing the obtained characteristic or characteristics with predetermined characteristics of the container types, wherein a container type is identified when the obtained characteristic or characteristics match or are within a predetermined range from matching one predetermined characteristic or one set of the predetermined characteristic for the container type.

9. The apparatus according to claim 8 wherein the handling station includes a sample identification means for identifying the sample by obtaining the identification indicator on the presented container and the obtained sample identification is used for the pathology analysis prescribed for the sample.

10. The apparatus according to claim 9 wherein the sample identification means is a bar code scanner and the sample identification indicator is a bar coded label fixed to the container.

11. The apparatus according to claim 8 wherein the container identification means is an image analyzer for capturing an image or images containing the one or more characteristics of the presented container and a light source for illuminating the presented container, said one or more characteristics including at least one of a dimension or dimensions of the presented container, one or more areas of the presented container and the color or colors of the cap of the container.

12. The apparatus according to claim 11 wherein the image analyzer is arranged to detect the level and/or volume of the sample or component of the sample for analysis and the handling station is provided with a controller which controls a rotatable container receiving means for positioning the presented container so that a window in the container allowing the sample to be visible externally is positioned before the image analyzer.

13. The apparatus according to claim 12 wherein the sample identification means produces a signal to the controller when the sample identification indicator is detected and the controller in turn stops the presented container at a predetermined position so that the window is before the analyzer.

14. The apparatus according to claim 8 wherein the apparatus comprises processing means having a storage device for storing said predetermined characteristic or set of characteristics relating to each container type.

15. The apparatus according to claim 14 wherein the processing means is arranged to access information relating to analysis prescribed for each sample online from a remote computer or from the storage device.

16. The apparatus according to claim 15 wherein the apparatus utilises the sample information for the determination of whether or not aspiration of the sample in an identified container is required, and if required the volume to be dispensed in one or each secondary container.

17. The apparatus according to claim 15 wherein the apparatus utilises the sample information for the determination of placement for the containers and/or secondary containers in a container distribution station.

18. The apparatus according to claim 1 wherein at least one of said containers has a cap and the apparatus includes a container distributor having a cap removal and replacement means including a container holder movable with respect to a rotatable cap engagement member, the holder being arranged to hold a capped container positioned thereat and to controllably move towards the cap engagement member for engaging therewith the cap of the capped container, and the cap removal and replacement means being arranged to rotate the engaged cap as the holder is controlled to move away from the cap engagement member thereby uncapping the capped container.

19. The apparatus according to claim 18 wherein the cap removal and replacement means is further arranged so that the holder can be controlled to move the uncapped container, sealed or open, towards the cap which is engaged with the cap engagement member, and the cap engagement is adapted to rotate the engaged cap as the holder is controlled to move the uncapped container towards the cap engaged with the cap engagement member for replacement of the cap onto the uncapped container.

20. The apparatus according to claim 18 wherein the cap engagement member has jaw parts arranged to grip onto the cap and the cap removal and replacement means is adapted to rotate the jaw parts as the holder is control led to move away from to the cap engagement member for uncapping the capped container.

21. The apparatus according to claim 19 wherein the cap engagement member has jaw parts arranged to grip onto the cap and the cap removal and replacement means is adapted to rotate the jaw parts as the holder is controlled to move away from to the cap engagement member for uncapping the capped container, and to rotate the engaged cap for replacement of the cap onto the uncapped container as the uncapped container is pushed onto the cap while the holder is controlled to move towards the cap engagement member.

22. The apparatus according to claim 1 wherein the apparatus includes a container distributor having sample aspiration and/or dispensing means for aspirating and/or dispensing volumetrically a predetermined portion of the sample in or to at least one of the containers, the sample aspiration and/or dispensing means includes a pipette tip holder for holding a plurality of pipette tips, a pipette probe, an articulated arm arranged for removing a pipette tip from the holder and place the pipette tip onto the probe, and a pipette tip removing means arranged to remove the pipette tip from the probe for deposition in a disposal receptacle.

23. The apparatus according to claim 22 wherein the apparatus includes a blockage detection means for detecting blockage of flow in a sample aspiration means including a pipette tip for aspirating volumetrically a predetermined portion of a sample in a container, a pipette tip controller is arranged to move the tip towards the sample in the container, the blockage detection means including a pressure sensitive module having a pump for aspiration of the sample through the tip, the blockage detection means being arranged to detect blockage in the tip and thereby to provide a warning signal and to cause the operation of the sample aspiration means to be arrested until the blockage has been resolved.

24. The apparatus according to claim 23 wherein the apparatus further includes a sample level detection means having a low pressure generating means for applying low pressure to the aspiration means, pressure sensor means for sensing the pressure in the aspiration means and an actuator for moving the tip towards the sample, the sample level being detected when the pressure as sensed by the sensor means exceeds a predetermined margin from said low pressure.

25. The apparatus according to claim 22 wherein the apparatus includes automatic labeling means for the application of an adhesive label to each said container with samples dispensed therein, the automatic labeling means includes one or more spools of adhesive labels, means for providing a sample identification indicator for identifying a dispensed sample on one of said adhesive labels, sample identification means for verifying that the applied indicator on said one label corresponds to the indicator of a container from which the sample is aspirated, and means for detecting errors in the indicators on the labeled container or the absence of a label.

26. The apparatus according to claim 22 wherein the apparatus includes hopper means for receiving and delivering one or more of the containers, and container alignment means arranged for aligning the containers from a substantially horizontal position to a vertical position with the open ends positioned to receive samples when the containers are delivered from said hopper means.

27. The apparatus according to claim 26 wherein the container alignment means includes a rotary magazine having circumferentially located compartments to hold substantially horizontally positioned containers, a sideways plunger member arranged in co-operation with the magazine and a guide positioned beneath the magazine to change the position of the containers released from the magazine from the horizontal to the vertical position, in operation the plunger member pushes a closed end of a container so that the displaced container released from the magazine falls into the guide in the vertical position, said co-operating plunger member when not in contact with a closed end, does not push a container which when released, falls into the guide in the vertical position.

28. The apparatus according to claim 22 wherein the apparatus includes a loading station having a conveyor arrangement for conveying the containers in position to be loaded onto a tube handling station, the conveyor arrangement having a movable conveyor surface on which carriers for carrying said containers can be placed, the conveyor surface having a first section arranged with a barrier dividing said first section into a buffer zone and a by-pass passage for the carriers, the buffer zone having an entrance and a diversion part is arranged adjacent to the entrance, in operation the diversion part diverts the carriers carrying containers into the buffer zone and empty carriers are allowed to continue to move into the by-pass passage.

29. The apparatus according to claim 28 wherein the diversion part is arranged so that when the buffer zone is full of carriers with tubes, other carriers with or without tubes continue to move into the by-pass passage.

30. The apparatus according to claim 29 wherein the buffer zone has a controllably actuable member positioned opposite to said entrance and the actuable member is controlled to push a carrier out of the buffer zone after the container on said carrier has been loaded onto the handling station or a rejected tube is placed on said carrier in the buffer zone.

31. The apparatus according to claim 30 wherein the conveyor surface has a second section arranged with another barrier dividing said second section into a reject zone for receiving carriers with rejected containers and a by-pass passage for other carriers, the reject zone having a diversion part arranged to divert the carriers carrying rejected containers into the reject zone and to allow empty carriers to continue to move into the by-pass passage.

32. A pathology sample distribution system having a plurality of containers of different types and the containers each containing a sample for pathology analysis a pathology specimen, the system comprising a loading station for loading said containers, a container handling station arranged to receive the containers in turn from the loading station, and a distribution station with areas or distribution holders marked for specific analyzing processes, the handling station including container sealing means for sealing each of said containers with samples dispensed therein, the container sealing means having a source of heat sensitive lamination tape, means for punching the tape to form a cap seal for each said container, means for placing said cap seal over a top of each said container and means for heating the can seal over each said container to cause the cap seal to seal each said container.

* * * * *